(12) United States Patent
Shirai et al.

(10) Patent No.: US 11,214,796 B2
(45) Date of Patent: *Jan. 4, 2022

(54) GENE EXPRESSION ANALYSIS ME1HOD USING TWO DIMENSIONAL CDNA LIBRARY

(71) Applicant: HITACHI, LTD., Tokyo (JP)

(72) Inventors: Masataka Shirai, Higashimurayama (JP); Hideki Kambara, Hachioji (JP); Kiyomi Taniguchi, Kunitachi (JP)

(73) Assignee: HITACHI, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/621,316

(22) Filed: Jun. 13, 2017

(65) Prior Publication Data

US 2017/0283796 A1    Oct. 5, 2017

Related U.S. Application Data

(63) Continuation of application No. 13/513,605, filed as application No. PCT/JP2010/071257 on Nov. 29, 2010, now abandoned.

(30) Foreign Application Priority Data

Dec. 4, 2009    (JP) .............................. JP2009-276883

(51) Int. Cl.
| | |
|---|---|
| C12N 15/10 | (2006.01) |
| G01N 33/543 | (2006.01) |
| C12Q 1/6809 | (2018.01) |
| C12Q 1/6837 | (2018.01) |
| C40B 40/08 | (2006.01) |
| C40B 50/06 | (2006.01) |

(52) U.S. Cl.
CPC ....... *C12N 15/1093* (2013.01); *C12Q 1/6809* (2013.01); *C12Q 1/6837* (2013.01); *C40B 40/08* (2013.01); *C40B 50/06* (2013.01); *G01N 33/54306* (2013.01); *G01N 2458/10* (2013.01)

(58) Field of Classification Search
CPC .............. C12N 15/1093; C12Q 1/6837; C12Q 1/6841; C12Q 1/6809; C40B 40/08
See application file for complete search history.

(56) References Cited

U.S. PATENT DOCUMENTS

| | | | | |
|---|---|---|---|---|
| 6,824,866 B1 * | 11/2004 | Glazer | .................. | B01J 19/0046 |
| | | | | 428/304.4 |
| 7,374,881 B2 | 5/2008 | Mitsuhashi | | |
| 2003/0124594 A1 | 7/2003 | Church et al. | | |
| 2003/0138941 A1 * | 7/2003 | Gong | .................... | B01L 3/5027 |
| | | | | 435/287.2 |
| 2005/0287549 A1 | 12/2005 | Nagai et al. | | |
| 2007/0281313 A1 * | 12/2007 | Taniguchi | ........... | C12N 15/1096 |
| | | | | 435/5 |
| 2009/0098541 A1 * | 4/2009 | Southern | ........... | B01L 3/502753 |
| | | | | 435/6.11 |
| 2010/0105104 A1 * | 4/2010 | Okano | .................... | B82Y 30/00 |
| | | | | 435/40.5 |

FOREIGN PATENT DOCUMENTS

| | | | | |
|---|---|---|---|---|
| JP | 2003-505694 | 2/2003 | | |
| JP | 2003-526331 | 9/2003 | | |
| JP | 2007-014297 | 2/2007 | | |
| JP | 2007/319028 | 12/2007 | | |
| WO | WO 2000/53812 | 9/2000 | | |
| WO | WO 2001/07915 | 2/2001 | | |
| WO | WO 2004/048928 | 6/2004 | | |
| WO | WO 2008/108004 | 9/2008 | | |
| WO | WO-2008108004 A1 * | 9/2008 | ............. | B82Y 30/00 |

OTHER PUBLICATIONS

Marcus et al.( Analytical chemistry 78.9 (2006): 3084-3089). (Year: 2006).*
Baner et al., Nucleic Acids Research, 2003, vol. 31, No. 17 e103; 1-7.
Lizardi et al., 1998, Nature Genetics 19: 225-232.
Jarvius et al., 2007, Molecular & Cellular Proteomics 6:1500-1509.
Taniguchi et al., Nature Methods, vol. 6, No. 7, Jul. 2009, p. 503-507, pg. Supplemental pp. 1-3.
Ute Romling et al., The impact of two-dimensional pulsed-field gel electrophoresis techniques for the consistent and complete mapping of bacterial genomes: refined physical map of Pseudomonas aeruginosa PAO, Nucleic Acids Research, 1991, pp. 3199-3206, vol. 19, No. 12.
Toshiko Omata et al., Mapping and Sequencing of RNAs without Recourse to Molecular Cloning: Application to RNAs of the Sabin 1 Strain of Poliovirus and Its Defective Interfering Particles[1], J. Biochem, 1986, pp. 207-217, vol. 99, No. 1.
David Zhang et al., Amplification of circularizable probes for the detection of target nucleic acids and proteins, Clinica Chimica Acta, 2006, pp. 61-70, vol. 363, No. 1-2.

* cited by examiner

*Primary Examiner* — Sahana S Kaup
(74) *Attorney, Agent, or Firm* — Baker Botts L.L.P.

(57) ABSTRACT

The present invention provides a method and/or means for collecting and analyzing an individual cell in a tissue, and at the same time, quantitatively monitoring the expression levels of various genes while keeping two-dimensional information in the tissue. Specifically, the present invention provides a method comprising preparing a cDNA library from mRNA while keeping two-dimensional cellular distribution information and obtaining the gene expression levels at any site or all sites at a level of single cell. More specifically, the present invention provides a method comprising preparing a cDNA library in a sheet-form from mRNA while keeping two-dimensional cellular distribution information and repeatedly using the cDNA library in the detection of the gene expression, thereby allowing measurement of the expression distribution for a number of genes at a high accuracy.

15 Claims, 23 Drawing Sheets

Specification includes a Sequence Listing.

5'AAATTGAGCCCGCAGCCTCCCGCTTCGCTCTCCTCCTGCTCTCGTGTTGCAGACAGTCAGCCGCATCTCTTTG
CGTCGCCAGCCGAGCCACATGCTCAGACACCATGGGGAAGGTGAAGGTCAACGGATTTGGTCG
TATTGGGCGCCTGGTCACCAGGGCTGCTTTTAACTCTGTAAAGTGGATATTGTTGCCATCAATGACCCC
TTCATTGACCTCAACTACATGGTTTACATGTTCCAATATGATTCCACCCATGGCAAATTCCATGGCACCG
TCAAGGCTGAGAACGGGAAGCTTGTCATCAATGGAAATCCCATCACCATCTTCCAGGAGCGAGATCCCTC
CAAATCAAGTGTGGGGCGATGCTGGCGTACGTCGTGAGTACGTCGTCTTCACCACCATGGAG
AAGGCTGGGGCTCATTTGCAGGGGGAGCCAAAGGGTCATCATCTCTGCCCCTCTGATGCCCCCA
TGTTCGTCATGGTGTGAACCATGAGAAGTATGACAACAGCCTCAAGATCATCAGACACTTGGTATCGTGAAGGACTCATGACC
CACCAACTGCTTAGCACACCCTGCCCAAGGTCATCCATGACTGTGATGGCCCCTCCGGAAACTGTGCGTGATGCC
ACAGTCCATGCCATCACTGCCACCCAGAAGACTCTCTGCCCTCTACTGGCGCTGCCAACGTGTGGGCAAGGTCATCCCTGA
GCGGGCTCTCCAGAACATCATCCCTGCCTCCGTGTCCAAGGCCATGGCCATGGCTCACTGGCCAGCTGCCAACGTGTCAGTGGTGGAC
GCTGAACGGGAAGCTCACTGGCATGGCCAAATATGATGAGCACCAGGTGGTCTCCTCTGACTTCAACAGCGACACCCACTCCTC
TGCCGTCTAGAAAAACCTGGGCTACACTGAGCACCAGGTGGTCTCCTCTGACTTCAACAGCGACACCCACTCCTC
TCAAGGGCATCCTGGGCTACACTGAGCACCAGGTGGTCATTGCCCTCAACGACCACTTCGTCAAGCTCATTTCCTGGTATGACAAC
CACCTTTGACGCTGGGGCTGGCATTGCCCTCAACGACCACTTCGTCAAGCTCATTTCCTGGTATGACAAC
GAATTTGGCTACAGCAACAGGGTGGTGGACCTCATGGCCCACATGGCCTCCAAGGAGTAAGACCCCTGGA
CCACCAGCCCCAACAGCAAGAGACAAGAGAGAGACCCTCACTGCCATGTAGACCCCTGCCACACTCA
GTCCCCACCACCACTGAATCTCCCCTCCTCCACAGTTGCCATGTAGACCCCTGCCACACTCA
GGGAGCCGCACCTTGTCATGTACCATCAATAAAGTACCCTGTGCTCAACC 3' (SEQ ID NO: 1)

FIG. 4

5'TCATGACCACAGTCCATGCCATCACTGCCACCCAGAGAAGACTGTGGATGGCCCCTCCGCTTAGCACCCTGGCCAAGGTCATCCATGACAACTTTGGTATCGTGTGGAAGGAC 3' (SEQ ID NO: 2)

FIG. 5

5'NH2-TCTCTCTCTCTCTCTCTCTCAGTCTTCTGGGTGGCAGTGATG3' (SEQ ID NO: 3)

FIG. 6

5'CACCCCTGGCCAAGGTCATCCA 3' (SEQ ID NO: 4)

FIG. 7

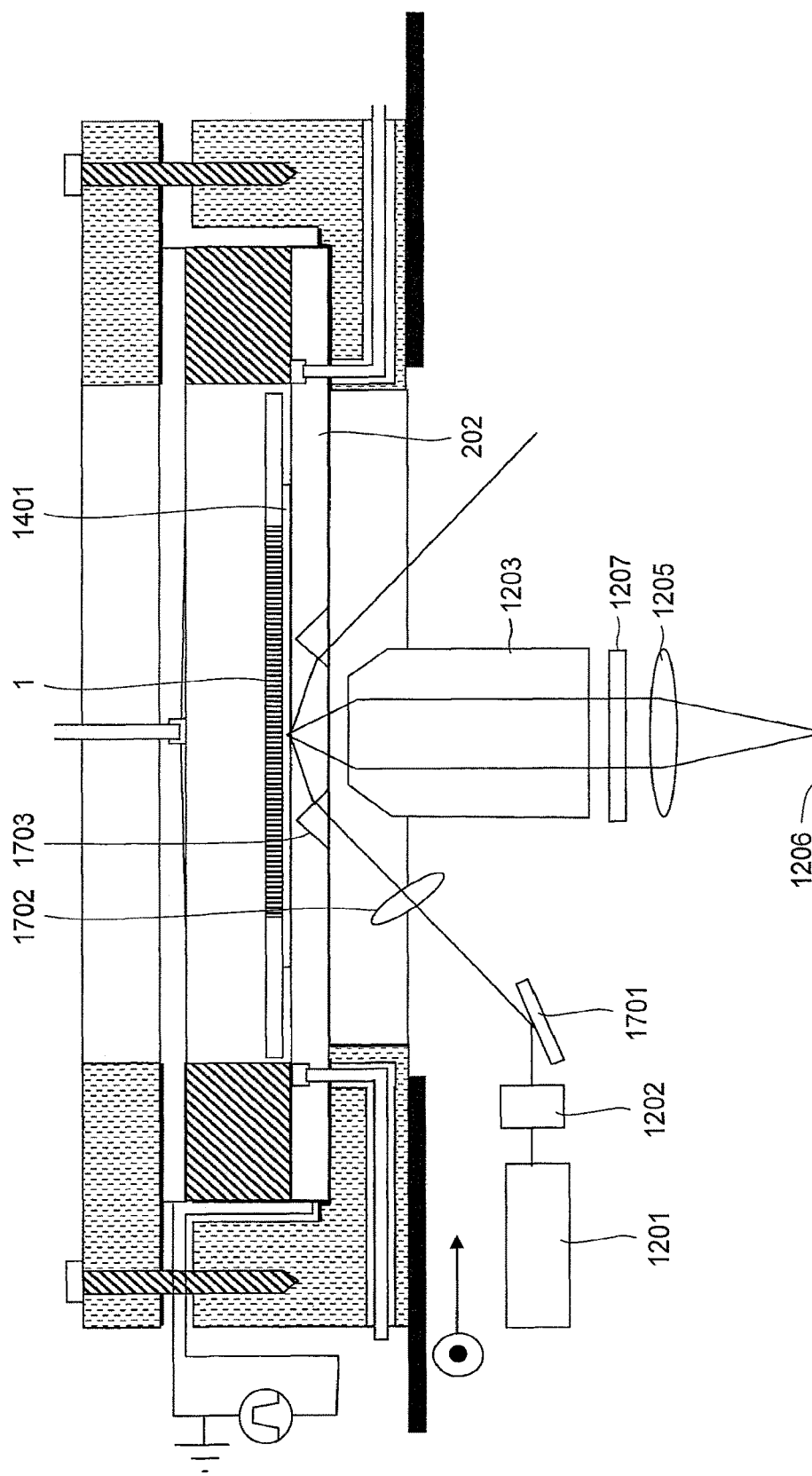

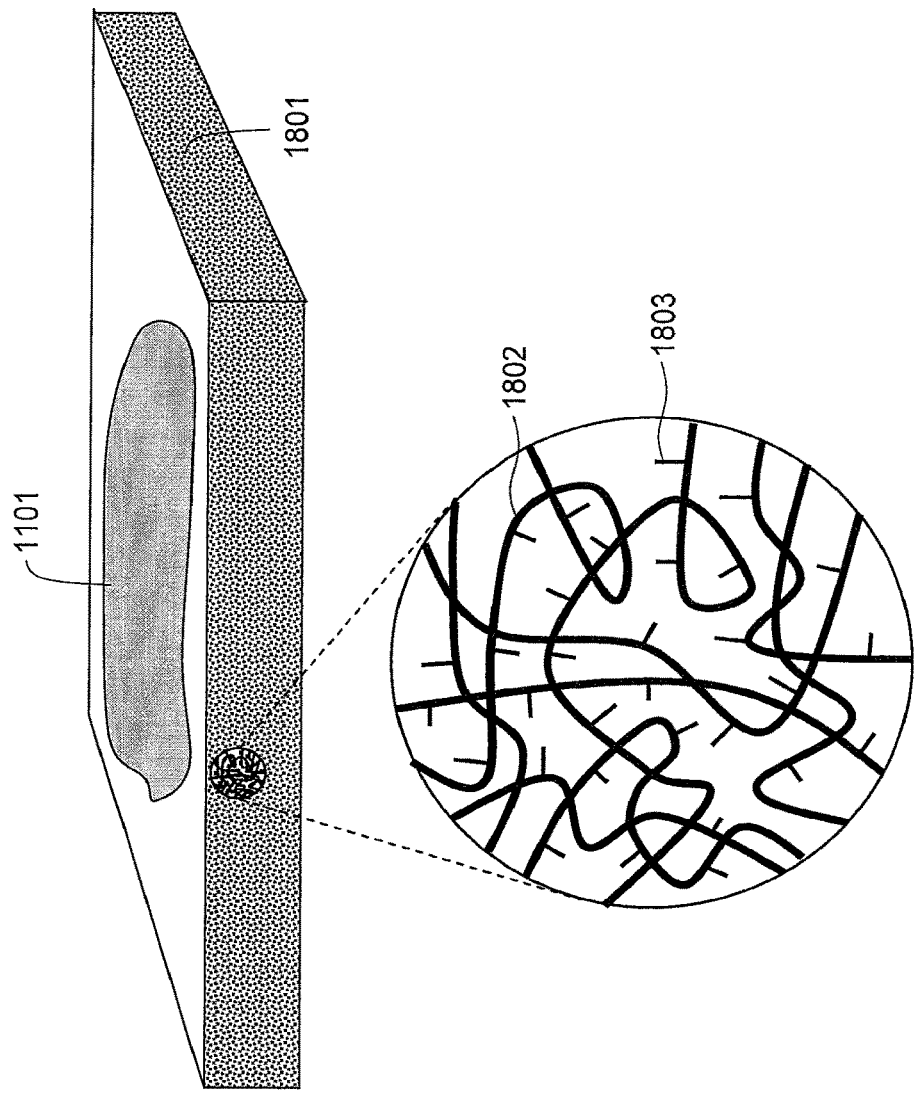

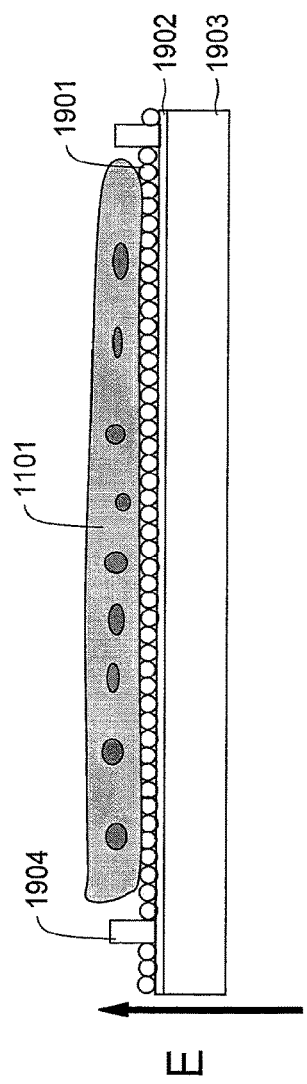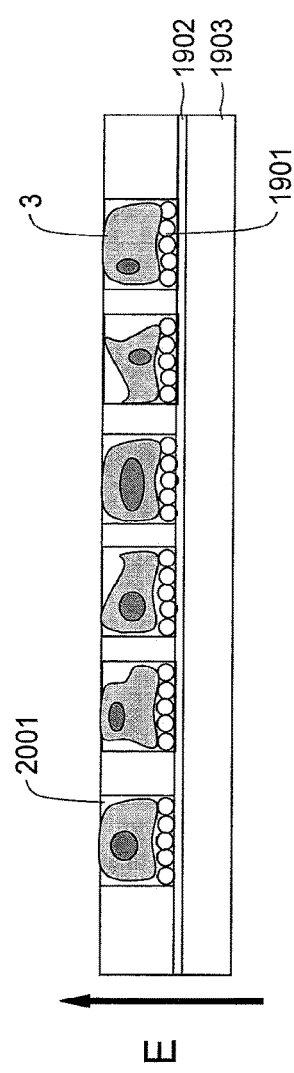

GENE EXPRESSION ANALYSIS METHOD USING TWO DIMENSIONAL CDNA LIBRARY

CROSS REFERENCE TO PRIOR APPLICATIONS

This application is a continuation of U.S. patent application Ser. No. 13/513,605, filed on Jun. 4, 2012, which is a U.S. National Phase application under 35 U.S.C. § 371 of International Application No. PCT/JP2010/071257, filed on Nov. 29, 2010, which claims benefit of priority to Japanese Application No. 2009-276883, filed on Dec. 4, 2009. The International Application was published in Japanese on Jun. 9, 2011 as WO 2011/068088 A1 under PCT Article 21(2). The contents of the above applications are hereby incorporated by reference.

BACKGROUND OF THE INVENTION

Technical Field

The present invention relates to a gene expression analysis method. More specifically, the present invention relates to a method of preparing a cDNA library from a nucleic acid contained in a sample and analyzing a gene expression profile in the sample.

Background Art

In gene expression analysis, mRNA is collected from cells and a complementary strand thereof, i.e., cDNA is prepared. This is amplified by a polymerase chain reaction (PCR) to increase the number of copies. Thereafter, a target is trapped by the corresponding site of a probe by use of a DNA probe array (DNA chip) and detected based on fluorescence. However, in such a method using PCR amplification and a DNA chip, accuracy of quantitative analysis is low, and thus, a highly accurate analysis method for a gene expression profile has been desired. With completion of human genome analysis, a need for quantitative analysis of gene expression has been increased. Recently, it has been desired to develop a quantitative analysis method by extracting mRNA from single cells. As a satisfactory quantitative analysis method, quantitative PCR is known. In this method, quantitative analysis is performed by preparing a reference sample having the same DNA sequence as that of a target, performing PCR amplification under the same conditions, and monitoring and comparing progress of amplification by a fluorescent probe. However, if the target is single cells, since the number of mRNAs originally present is low, it is difficult to quantitatively analyze them. In addition, if expression of a plurality of genes is to be quantitatively analyzed, a sample should be divided into portions and each of them should be independently analyzed quantitatively. If the number of target genes is large and genes of low expression level are included, some of the genes cannot be measured due to the division of the sample.

Under the circumstances, the group of the present inventors conceived a method (JP Patent Publication No. 2007-319028 A): all mRNAs are converted into cDNAs and allowed to be retained on beads to prepare a cDNA library (cDNA assembly containing all cDNAs), which is used in quantitative analysis. They showed that a measurement error caused by the division of the sample when a gene of low expression level is measured can be avoided by repeatedly using a cDNA library, thereby accurately determining expression levels of plurality of genes contained in single cells. Whereas, in the case of a biological tissue, mRNA has been collected from a number of cells and subjected to analysis. At present, this is only one technique available for the analysis. Expression of a gene while keeping a two-dimensional form of a biological tissue is analyzed by monitoring about one or two mRNAs by use of fluorescent probes.

SUMMARY OF INVENTION

In regenerative medicine, diagnosis based on a gene or fundamental understanding of life phenomena, analyzing not only average gene expression levels in a tissue but also the gene expression levels in individual cells contained in the tissue are important. To attain this, not only analyzing cells by collecting them one by one but also quantitatively monitoring the expression of various genes while keeping a two-dimensional information of a tissue are desired. However, a satisfactory method has not yet been developed up to present. If the number of target genes is one or two, gene expression in the tissue can be observed by use of a label using fluorescent probes; however, the expression levels of a number of genes cannot be observed. Ideally, if a gene (mRNA) functioning in the biological tissue constituting a two-dimensional or three dimensional structure can be measured at a single cell level while keeping the positional information of/within the cell, various phenomena taking place within a living organism can be elucidated more specifically including cellular interaction. If so, conceivably, a big impact can be given to the bioscience field, in particular, a medical field or a drug development field.

As described above, it has been demanded that living activity is elucidated based on information obtained from a single cell from average information of a number of cells, and further that not only a single cell but also a large number of cells are analyzed one by one.

The present inventors intensively studied with a view to solving the aforementioned objects. As a result, we have prepared a cDNA library from mRNA while keeping two-dimensional cell distribution information in a living tissue, and have developed a method for analyzing the expression levels of genes present at any sites including arbitrary selected sites or target sites at the level of positional resolution in a single cell. More specifically, we have found that the aforementioned objects can be solved by preparing a cDNA library sheet, which has a correlation with the positional information of each cell or a cell site within a two-dimensional tissue, and using it in gene expression analysis.

More specifically, the present invention encompasses the following items (1) to (27).

(1) A method for analyzing a gene expression profile, comprising the steps of:
(a) hybridizing a test nucleic acid in a sample with a nucleic acid probe which has been two-dimensionally distributed and immobilized onto a support;
(b) synthesizing cDNA having a complementary sequence to the sequence of the test nucleic acid and preparing a two-dimensional cDNA library on the support; and
(c) detecting gene expression in the sample by using the two-dimensional cDNA library.

(2) The method according to item (1), wherein the sample contains a plurality of cells and the gene expression profile is analyzed for each of the cells.

(3) The method according to item (1) or (2), wherein the sample contains a plurality of cells, the gene expression profile is analyzed for each of the cells and the gene expression profiles of cells are compared.

(4) The method according to any one of items (1) to (3), wherein the sample is a biological tissue sample, and a two-dimensional cDNA library is prepared while keeping two-dimensional positional information of cells contained in the biological tissue sample.

(5) The method according to any one of items (1) to (3), wherein the sample is a biological tissue sample and a two-dimensional cDNA library is prepared while keeping two-dimensional positional information within cells contained in the biological tissue sample.

(6) The method according to item (4) or (5), wherein the biological tissue sample is a tissue section sample and a test nucleic acid in the tissue section sample is transferred to the support to hybridize with the nucleic acid probe.

(7) The method according to item (6), wherein the transfer of the test nucleic acid to the support is performed by electrophoresis.

(8) The method according to any one of items (1) to (7), wherein the sample is an array of cells two-dimensionally held.

(9) The method according to any one of items (1) to (8), wherein the test nucleic acid is selected from the group consisting of messenger RNA (mRNA), non-coding RNA (ncRNA) and DNA, and fragments thereof.

(10) The method according to item (9), wherein the test nucleic acid is mRNA and the nucleic acid probe is a DNA probe containing a poly-T sequence.

(11) The method according to any one of items (1) to (10), wherein the support is at least one selected from the group consisting of a sheet, a membrane, a gel thin film, a capillary plate and beads.

(12) The method according to any one of items (1) to (11), wherein the support has a plurality of micro spaces two-dimensionally segmented.

(13) The method according to item (12), wherein the interval between the micro spaces is smaller than the size of a cell.

(14) The method according to item (12) or (13), wherein the two-dimensional cDNA library retains cDNAs in a plurality of micro spaces two-dimensionally segmented in the support.

(15) The method according to any one of items (1) to (14), further comprising transferring the cDNAs retained in the two-dimensional cDNA library to a second support to hybridize with a nucleic acid probe which has a complementary sequence to the cDNA and a fragment thereof and has been two-dimensionally distributed and immobilized onto the second support, thereby preparing a second two-dimensional cDNA library.

(16) The method according to any one of items (1) to (15), further comprising generating a nucleic acid fragment corresponding to cDNA retained in the two-dimensional cDNA library, transferring the nucleic acid fragment to the second support while keeping the two-dimensional positional information of the two-dimensional cDNA library, thereby preparing a second two-dimensional cDNA library.

(17) The method according to item (16), wherein the nucleic acid fragment corresponding to cDNA contains a complementary sequence of the cDNA.

(18) The method according to item (16), wherein the nucleic acid fragment corresponding to cDNA contains a complementary sequence of cDNA and a known sequence unrelated to the cDNA sequence.

(19) The method according to any one of items (1) to (18), wherein a labeled nucleic acid probe specific to the gene to be detected is hybridized with cDNA retained in the two-dimensional cDNA library and gene expression is detected based on the label.

(20) The method according to item (19), wherein the label is a fluorescent label or a chemiluminescent label.

(21) The method according to any one of items (1) to (18), wherein a nucleic acid probe specific to the gene to be detected is hybridized with cDNA retained in the two-dimensional cDNA library; a nucleic acid sequence contained in the nucleic acid probe is subjected to an amplification reaction; and gene expression is detected based on an amplified product.

(22) The method according to item (21), wherein the amplification reaction is a polymerase chain reaction (PCR).

(23) The method according to any one of items (1) to (18), wherein a nucleic acid padlock probe specific to the gene to be detected is hybridized with cDNA retained in the two-dimensional cDNA library; the padlock probe hybridized is subjected to a ligation reaction to form a ring form probe; a rolling circle amplification (RCA) reaction is performed with the ring form probe as a template; and gene expression is detected based on an amplified product.

(24) The method according to any one of items (21) to (23), wherein the amplified product is detected by use of fluorescence or chemiluminescence.

(25) The method according to any one of items (1) to (24), wherein the two-dimensional cDNA library is repeatedly used to perform the step of detecting gene expression.

(26) The method according to any one of items (1) to (25), further comprising comparing the results from the detection of gene expression in the two-dimensional cDNA library with two-dimensional positional information of the sample to obtain correlation data between a specific position in the sample and gene expression.

(27) A method for analyzing a profile of a molecule contained in a sample, comprising the steps of:

(a) binding a test molecule in a sample to an antibody or aptamer which has been two-dimensionally distributed and immobilized onto a support;

(b) forming a ring probe specific to binding of the test molecule to the antibody or aptamer, by use of a proximity ligation method;

(c) preparing a two-dimensional cDNA library by using the ring probe or a nucleic acid fragment generated with the ring probe as a template; and (d) detecting the presence of a molecule in the sample by using the two-dimensional cDNA library.

(28) The method according to item (27), wherein the molecule is a protein.

The present invention provides a method for analyzing a gene expression profile. The method of the present invention enables to analyze expression of a gene in a sample with its two-dimensional positional information. Furthermore, in the method of the present invention, since genes expressed in a sample can be all converted into cDNAs to construct a cDNA library, gene expression can be simply and efficiently detected. Therefore, the present invention is useful for the fields of e.g., cell function analysis, biological tissue analysis, diagnosis of diseases and drug development. Particularly, by applying the present invention to pathological pieces so far collected, elucidation of various diseases, establishment of diagnostic approach, or development of pharmaceutical products, etc. can be performed.

BRIEF DESCRIPTION OF DRAWINGS

FIG. 4 shows an example of a target sequence (SEQ ID NO: 1).

FIG. 5 shows an example of the sequence (SEQ ID NO: 2) of a padlock probe.

FIG. 6 shows an example of the sequence (SEQ ID NO: 3) of common DNA probe I.

FIG. 7 shows an example of the sequence (SEQ ID NO: 4) of common DNA probe II.

FIG. 17 shows an example of an optical system based on evanescent-excitation used for measuring fluorescence.

FIG. 18 shows an example of a method for preparing a cDNA library in a membrane.

FIG. 19 shows an example of a method for preparing a cDNA library on beads.

FIG. 20 shows another example of a method for preparing a cDNA library on beads.

DETAILED DESCRIPTION OF THE INVENTION

Figure 1:
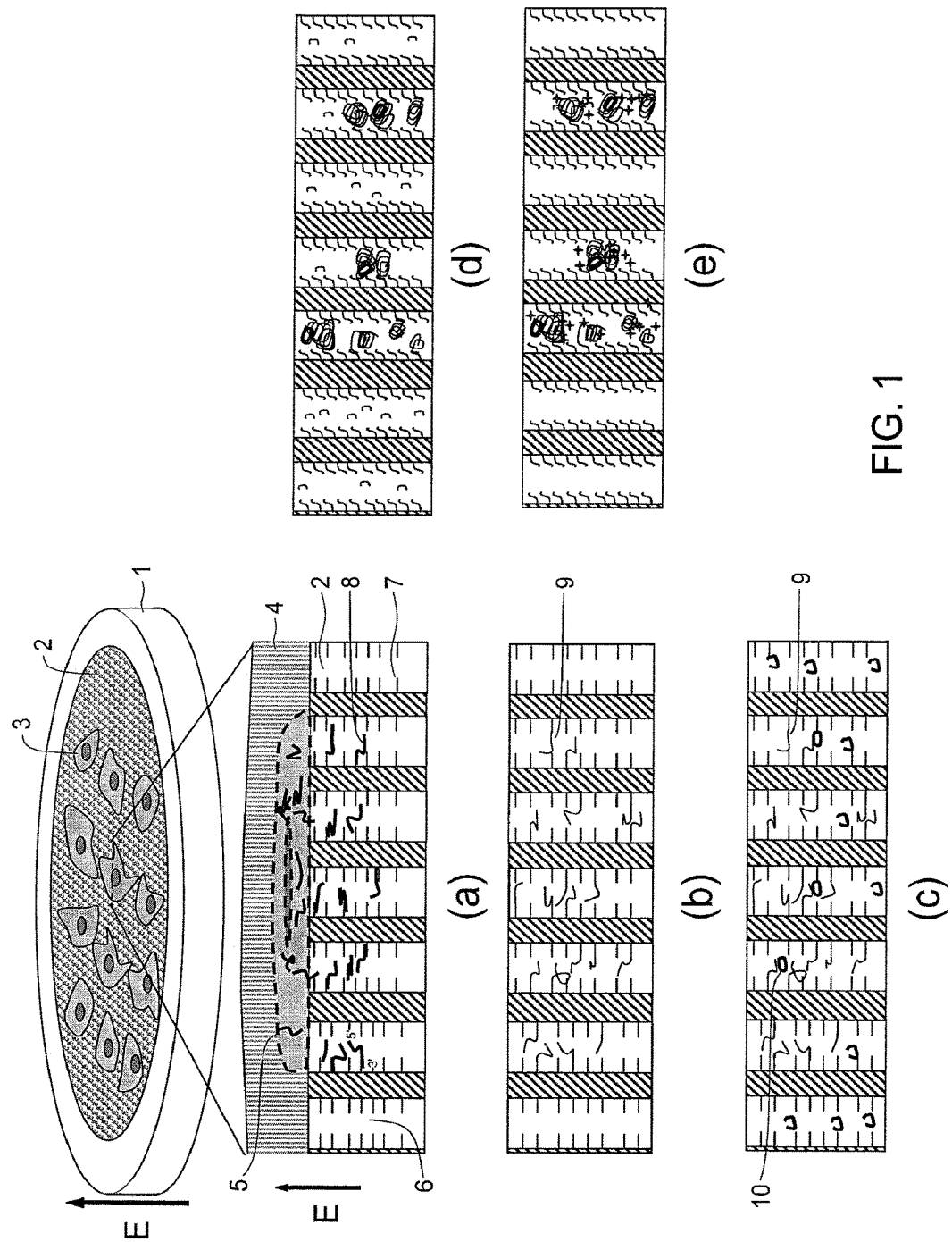
FIG. 1 is a schematic view illustrating a method for preparing a two-dimensional cDNA library in a pore array sheet.

The present invention will be described in detail below. The present application claims a priority to Japanese Patent Application No. 2009-276883 filed Dec. 4, 2009, the contents described in the specification and/or drawings of which are incorporated herein by reference.

The method for analyzing a gene expression profile according to the present invention contains the following steps:

(a) hybridizing a test nucleic acid in a sample with a nucleic acid probe which has been two-dimensionally distributed and immobilized onto a support;

(b) synthesizing cDNA having a complementary sequence to the sequence of the test nucleic acid and preparing a two-dimensional cDNA library on the support; and (c) detecting gene expression in the sample by using the two-dimensional cDNA library.

In the present invention, "analyzing a gene expression profile" refers to quantitatively analyzing gene expression in a sample (cell, tissue section, etc.), analyzing gene-expression distribution in a sample, and/or obtaining the correlation data between a specific position in a sample and gene expression level.

The sample is not particularly limited as long as the sample is derived from a living organism whose gene expression profile is to be analyzed. Any sample such as a cell sample, a tissue sample and a liquid sample can be used. Specific examples thereof include a sample constituted of a single cell, a sample containing a plurality of cells, a tissue section sample, and a sample in the form of an array of a plurality of cells two-dimensionally retained.

Furthermore, the living organism from which a sample is derived is not particularly limited. Samples derived from any living organism including vertebrates (for example, mammals, birds, reptiles, fish and amphibians) and invertebrates (for example, insects, eelworms, crustacea), protists, plants, fungi, bacteria and viruses can be used.

In the method of the present invention, for example, where a sample contains a plurality of cells, a gene expression profile for each of the cells can be analyzed. Furthermore, for example, where a sample contains a plurality of cells, a gene expression profile for each of the cells can be analyzed and gene expression profiles of the cells can be compared.

In the method of the present invention, it is preferable that, for example, the sample is a biological tissue sample, and that a two-dimensional cDNA library is prepared while keeping two-dimensional positional information of cells contained in the biological tissue sample. Alternatively, it is preferable that the sample is a biological tissue sample, and that a two-dimensional cDNA library is prepared while keeping two-dimensional positional information within cells contained in a biological tissue sample. As the biological tissue sample, a tissue section sample can be used. By transferring a test nucleic acid in the tissue section sample to a support, it can hybridize with a nucleic acid probe. The test nucleic acid can be transferred to the support, for example, by using electrophoresis.

In the method of the present invention, as a test nucleic acid, messenger RNA (mRNA), non-coding RNA (ncRNA) and DNA, and fragments thereof can be used. For example, a test nucleic acid can be prepared by extracting the nucleic acid contained in a sample by a method known in the art. For example, cells are lysed by a proteolytic enzyme such as Proteinase K, a chaotropic salt such as guanidine thiocyanate and guanidinium hydrochloride, a surfactant such as Tween and SDS or a commercially available cell lysis reagent, and extracting a nucleic acid, i.e., DNA and RNA, contained therein. If mRNA is used as a test nucleic acid, DNA of the nucleic acids extracted by the cell lysis described above is digested with DNase to obtain a sample containing RNA alone as a nucleic acid.

Furthermore, the nucleic acid probe to be used is not particularly limited as long as it can hybridize with these test nucleic acids and trap them, and is known to those skilled in the art. For example, if the test nucleic acid is mRNA, a DNA probe having a poly-T sequence is preferably used as a nucleic acid probe. The DNA probe having a poly-T sequence, in other words, oligo (dT), is preferably synthesized by a conventional method. The polymerization degree of oligo (dT) is acceptable as long as the oligo (dT) hybridizes with a poly-A sequence of mRNA to trap mRNA by a support having the oligo (dT) immobilized thereon.

The support is not particularly limited, and may be prepared from a material generally used for preparing a cDNA library in the art. Examples of the support include a sheet, a membrane, a gel thin film, a capillary plate, beads and a film. Examples of the material thereof include metals such as gold, silver, copper, aluminium, tungsten, molybdenum, chromium, platinum, titanium and nickel; alloys such as stainless steel, hastelloy, inconel, monel and duralumin; silicon; glass materials such as glass, quartz glass, fused quartz, synthetic quartz, alumina, sapphire, ceramics, forsterite and photosensitive glass; plastics such as a polyester resin, polystyrene, a polyethylene resin, a polypropylene resin, an ABS resin (Acrylonitrile Butadiene Styrene resin), nylon, an acryl resin, a fluorine resin, a polycarbonate resin, a polyurethane resin, a methylpentene resin, a phenol resin, a melamine resin, an epoxy resin and a vinyl chloride resin; agarose, dextran, cellulose, polyvinyl alcohol, nitrocellulose, chitin and chitosan. For example, if a sheet is used as a support, the sheet can be prepared from, for example, alumina and glass. Furthermore, if a gel thin film is used as the support, the gel thin film can be prepared from, for example, an acryl amide gel, gelatin, a modified polyethylene glycol, a modified polyvinyl pyrrolidone or hydro gel. If a membrane is used as the support, for example, cellulose acetate, nitrocellulose or a membrane formed of a mixture thereof and a nylon membrane can be used. If beads are used as a support, beads can be prepared from a resin material (polystyrene, etc.), an oxide (glass, etc.), a metal (iron, etc.), Sepharose and a combination thereof.

In the two-dimensional cDNA library herein, in order to retain cDNA while keeping two-dimensional positional information, a support preferably has a plurality of micro spaces two-dimensionally segmented. Such plural micro spaces can be set up, for example, by forming pores in a sheet, a gel thin film or a capillary plate or by spreading beads in spaces segmented like cells. The interval between the micro spaces in the support is preferably smaller than the size of a cell.

A nucleic acid probe can be immobilized onto a support in accordance with any method known in the art. For example, a nucleic acid probe can be immobilized onto e.g., a surface of a support, interior of pores or a membrane fiber by use of covalent bonding, ion bonding, physical adsorption or biological binding (for example, binding of biotin and avidin or streptoavidin, and antigen-antibody binding). Alternatively, a nucleic acid probe can be immobilized onto a support via a spacer sequence.

A nucleic acid probe can be immobilized onto a support via covalent bonding, for example, by introducing a functional group into the nucleic acid probe, introducing a functional group reactive to the functional group to the surface of the support, and allowing the functional groups to react. For example, a covalent bond can be formed by introducing an amino group into a nucleic acid probe and introducing an active ester group, an epoxy group, an aldehyde group, a carbodiimide group, an isothiocyanate group or an isocyanate group to a support, or by introducing a mercapto group into a nucleic acid probe and introducing an active ester group, a maleimide group or a disulfide group into a support. As one of the methods for introducing a functional group into the surface of a support, a method of treating a support with a silane coupling agent having a desired functional group may be used. Examples of the coupling agent that can be used include γ-aminopropyltriethoxysilane, N-β-(aminoethyl)-γ-aminopropyltrimethoxysilane, and N-β-(aminoethyl)-β-aminopropylmethyldimethoxysilane. As another method for introducing a functional group serving as a binding site into a support, a plasma treatment may be used. Furthermore, as a method for immobilizing a nucleic acid probe to a support by physical adsorption, a method of electrostatically binding a nucleic acid probe to a support treated with a polycation (polylysine, polyallyl amine, polyethylene imine, etc.) by use of charge of the nucleic acid probe may be used.

It may be preferable that surface coating is applied to a support so as for other substances (nucleic acid, protein, etc.) not to adsorb thereon.

To hybridize a test nucleic acid in a sample with a nucleic acid probe immobilized onto a support, the test nucleic acid in a sample is extracted as mentioned above and brought into contact with the support. At that time, for example, taking advantage of negative charge of the nucleic acid, an electric field is applied to a sample containing a test nucleic acid and a support to electrophoretically transfer the test nucleic acid to the proximity of the nucleic acid probe immobilized onto a support.

The hybridization reaction can be carried out by incubating a support having a nucleic acid probe immobilized thereto and a sample containing a test nucleic acid in the sample. The incubation for such hybridization is performed at a temperature of 70° C. for about 5 minutes while gently stirring and thereafter the temperature is preferably reduced slowly to room temperature at a rate of about 0.1° C./second. After the hybridization reaction, unbound components are preferably washed out from the support.

After the test nucleic acid and the nucleic acid probe are hybridized, cDNA having a complementary sequence to whole or part of the sequence of the test nucleic acid is synthesized. The complementary strand can be synthesized by a known method in the art. For example, if the test nucleic acid is mRNA or ncRNA, cDNA can be synthesized, for example, by a reverse transcription reaction using reverse transcriptase. Whereas, if the test nucleic acid is DNA, cDNA can be synthesized, for example, by a replication reaction using a polymerase. After the synthesis reaction, the test nucleic acid is digested and removed, for example, with RNase. As a result, a two-dimensional cDNA library containing cDNA corresponding to the test nucleic acid may be constructed in/on the support. In the two-dimensional cDNA library prepared, cDNA is retained, preferably in a plurality of micro spaces two-dimensionally segmented in the support.

After synthesis of cDNA, a washing/removing operation is applied to the two-dimensional cDNA library (support) to remove residual reagents such as a cell lysis reagent and DNase. Owing to this, the following step of detecting gene expression can be carried out without being inhibited.

Furthermore, optionally, by transferring cDNA contained in the two-dimensional cDNA library prepared as mentioned above or by producing a nucleic acid fragment corresponding to cDNA contained in the two-dimensional cDNA library, information of cDNA contained in the original two-dimensional cDNA library can be transferred to another two-dimensional cDNA library.

For example, transferring a cDNA retained in the two-dimensional cDNA library to a second support is made by a method of two-dimensionally distributing a nucleic acid probe having a complementary sequence to the cDNA and a fragment thereof in a second support and immobilizing it, and hybridizing the nucleic acid probe immobilized onto the second support with cDNA retained in the original two-dimensional cDNA library. In this manner, the second two-dimensional cDNA library can be prepared.

Furthermore, for example, in producing the nucleic acid fragment corresponding to cDNA contained in the two-dimensional cDNA library, a nucleic acid fragment containing a complementary sequence of the cDNA may be produced, or the nucleic acid probe specific to the cDNA may be hybridized and used as a nucleic acid fragment, or a nucleic acid fragment containing a cDNA complementary sequence and a known sequence unrelated to the cDNA sequence may be produced. The nucleic acid fragment thus produced is transferred to a second support while keeping two-dimensional positional information of the two-dimensional cDNA library, thereby preparing a second two-dimensional cDNA library.

The two-dimensional cDNA library (including a second two-dimensional cDNA library) prepared as mentioned above can be repeatedly used by washing after individual operations. Thus, a gene expression detection step (described later) using the same two-dimensional cDNA library can be repeated multiple times.

Subsequently, gene expression is detected in a sample by use of the two-dimensional cDNA library (including a second two-dimensional cDNA library) prepared as described above. In the present invention, the "detection" includes detection of presence or absence of gene expression as well as quantitative detection of gene expression.

As one of the methods for detecting gene expression, a method for detecting gene expression by hybridizing a labeled nucleic acid probe specific to a target gene to be detected with a cDNA retained in the two-dimensional cDNA library, and detecting gene expression based on the label, is known. The nucleic acid probe which can be used in such detection can be appropriately designed by those skilled in the art. As the label to be used, any label can be used as long as it is known in the art. Examples thereof include fluorescent labels (Cy3, fluorescein isothiocyanate (FITC), tetramethylrhodamineisothiocyanate (TRITC) etc.), chemiluminescent labels (luciferin etc.), enzyme labels (peroxidase, β-galactosidase, alkaline phosphatase etc.) and radioactive labels (tritium, iodine$^{125}$ etc.).

Furthermore, as another method, a method for detecting gene expression by hybridizing a nucleic acid probe specific to a target gene to be detected with cDNA retained in the two-dimensional cDNA library, subjecting a nucleic acid sequence contained in the nucleic acid probe to an amplification reaction, and detecting gene expression based on the amplified product, is known. As the amplification reaction mentioned above, any method can be used as long as it is known in the art. Examples thereof include a polymerase chain reaction (PCR), a rolling circle amplification (RCA) reaction, a Nucleic Acid Sequence-Based Amplification (NASBA) method and a Loop-Mediated Isothermal Amplification (LAMP) method. Furthermore, the nucleic acid probe to be used can be appropriately designed by those skilled in the art depending upon the amplification reaction to be employed. For example, if a rolling circle amplification (RCA) reaction is employed as the amplification reaction, a nucleic acid padlock probe specific to a target gene to be detected is hybridized with cDNA retained in the two-dimensional cDNA library. The padlock probe hybridized may be formed into a ring form probe through a ligation reaction. An RCA reaction may be performed with the ring form probe as a template. Based on the amplified product, gene expression can be detected. Furthermore, the above amplification reaction process may contain introducing a repeat sequence to an end of cDNA.

Such an amplified product can be detected by any method known in the art. For example, a label can be attached to a substrate (base) to be used in the amplification reaction to detect an amplification product based on the label. Alternatively, by using a labeled nucleic acid probe capable of specifically binding to the resultant amplified product, an amplified product can be detected based on the label of the nucleic acid probe bound thereto. Examples of the label to be used are the same as mentioned above.

The detection based on the label can be performed in accordance with a method and apparatus known in the art. For example, a fluorescent label and a chemiluminescent label are excited by an appropriate light laser, and fluorescence emission can be detected and quantified based on counting by an optical system, a fluorescent microscope, a plate reader etc. Furthermore, if an enzyme label is used, a substrate capable of developing color by enzymatic degradation is added, and detection and quantification can be made by optically measuring the amount of degraded substrate. If a radioactive label is used, the dose of radiation emitted from the radioactive label can be measured by a scintillation counter, etc. In the method of the present invention, gene expression can be quantitatively analyzed by using fluorescence or chemiluminescence, i.e., counting the number of positions from which the light signal is emitted. Furthermore, as a specific example, gene expression can be quantitatively analyzed by performing an amplification reaction as mentioned above based on cDNA derived from a single test nucleic acid, introducing or immobilizing the resultant amplified product into a micro reaction cell of 1 µl or less, and counting the number of spots from which fluorescence or chemiluminescence is emitted.

Another method for detecting gene expression includes hybridizing a nucleic acid probe specific to a target gene to be detected with cDNA retained in the two-dimensional cDNA library, subsequently hybridizing the nucleic acid probe alone with a second nucleic acid probe specific to the nucleic acid probe immobilized onto an electrode, and measuring a potential change of an electrode due to the hybridization.

In the present invention, the results from the detection of gene expression in the two-dimensional cDNA library obtained as mentioned above can be compared to two-dimensional positional information of a sample to obtain correlation data between the specific position in the sample and gene expression. Examples of such two-dimensional positional information of a sample include a microscopic image of a cell sample or a tissue section sample, and a fluorescent image or a chemiluminescent image obtained by other labeling methods.

In another aspect, the method for analyzing a profile of a molecule contained in a sample according to the present invention, comprises the following steps:

(a) binding a test molecule in a sample to an antibody or aptamer which has been two-dimensionally distributed and immobilized onto a support;

(b) forming a ring probe specific to binding of the test molecule to the antibody or aptamer, by use of a proximity ligation method;

(c) preparing a two-dimensional cDNA library by using the ring probe or a nucleic acid fragment generated with the ring probe as a template; and (d) detecting the presence of a molecule in the sample by using the two-dimensional cDNA library.

In this method, in place of hybridizing a test nucleic acid in the sample with a nucleic acid probe as described above, a test molecule in a sample is bound to a ligand (antibody or aptamer etc.,) capable of specifically binding to the test molecule to form a ring probe in accordance with a proximity ligation method, thereby preparing a two-dimensional cDNA library. In the present invention, examples of the molecule to be detected include any molecules such as proteins, peptide nucleic acids, macromolecules (polymers) and low molecules. Since a test molecule is trapped by a support by means of a specific binding, the test molecule may preferably be one to which a ligand (a specifically binding ligand) specifically binds. For example, when a protein is selected as the test molecule, an antibody or an aptamer can be selected as a specifically binding ligand.

Preparation of a two-dimensional cDNA library using the proximity ligation method will be more specifically described in Example 8.

According to the method of the present invention mentioned above, a two-dimensional cDNA library can be prepared by converting a gene or molecule expressing in all cells within a biological tissue into cDNA while keeping positional information of cells within the tissue. Therefore, expression of a gene in any site of concern or expression of the gene in all sites can be understood, and various information so far unable to obtain, such as how genetic information is spread within the tissue, can be visualized. Furthermore, if a tissue is sliced to obtain a slice piece sample, and a two-dimensional cDNA library of the slice piece is prepared and then gene expression is checked, three dimensional distribution data of gene expression can also be obtained. These are different from conventional fluorescence detection methods dealing with a small number of genes, and can simply and efficiently provide information of a great number of genes. Furthermore, based on the analysis results on the gene expression profile obtained by the present invention, it is expected that a great deal of new information can be provided including genetic information flow and effect of a stimulus on the tissue.

EXAMPLES

The present invention will be more specifically described by way of Examples below. It may be understood that the following Examples should not be construed as limiting the invention.

Example 1

This Example is an example of using a two-dimensional cDNA library sheet, which was constructed in a pore array sheet, from sheet-type cells while keeping positional information of mRNA contained therein. Hereinafter, a sheet in which a number of pores are two-dimensionally formed will be referred to as a pore array sheet and a pore array sheet in which a cDNA library is formed will be referred to as a cDNA library sheet. A conceptual figure of an example of the method is shown in FIG. 1.

This method contains: a step of extracting and trapping mRNA, while keeping cell positional information, by a DNA probe within a sheet (FIG. 1 (a)); a step of preparing a cDNA library by reverse transcription within the sheet (FIG. 1 (b)); a step of determining presence of a target cDNA by hybridizing a DNA probe (padlock probe), which is capable of hybridizing with the target cDNA at both ends, with the target cDNA and preparing a ring-form DNA probe (referred to as a ring probe) through a ligation reaction (this is one of the methods for determining a gene expression profile accompanying the above step) (FIG. 1 (c)); a step of a DNA amplification (referred to as RCA (Rolling Circle Amplification)) for preparing DNA consisting of specific sequences which are tandemly connected, by synthesizing a complementary strand through hybridization with the ring probe and amplifying the complementary sequence to the ring probe (FIG. 1 (d)); and a step of quantifying (counting) genes by hybridizing a fluorescent probe having a partial sequence complementary to the DNA tandemly connected and measuring fluorescence, more specifically, by counting spots emitting light (FIG. 1 (e)).

First, as a pore array sheet for preparing a cDNA library, a pore array sheet obtained by anodic oxidation of alumina was used. In this Example, a case of using a sheet 1 having a pore of 200 nm in diameter and having a thickness of 60 μm and a diameter of 25 mm, will be described as an example; however, the shape of the pore array sheet is not limited to this. Such a sheet can be prepared through anodic oxidation by researchers themselves, or a product having a pore of 20 nm to 200 nm in diameter is commercially available. As the pore array sheet, e.g., a monolith sheet formed of porous glass, a capillary plate prepared by bundling capillaries and slicing it, a nylon membrane or a gel thin film can also be used. Pores 2 formed in the sheet 1 pierce through the sheet 1 in the thickness direction. Pores are completely mutually independent. The surface is hydrophilic, adsorption of proteins to the surface is extremely low and thus an enzyme reaction efficiently proceeds. First, the surface of the pore array sheet is treated with a silane coupling agent and DNA probes 7 are immobilized onto the pore surfaces. Immobilized probes are present on the surface at a ratio of one per area of 30 to 100 $nm^2$ in average, 4 to $10 \times 10^6$ of DNA probes are immobilized per single pore. Next, in order to prevent surface adsorption, the surface is coated with a surface coating agent. The surface coating may be performed simultaneously with immobilization of the probe. As the probe, a DNA probe having poly-T sequence (25 mer) was used. The probe density is set so as to trap 100% of mRNAs passing through the space of the pore.

Next, mRNA is extracted from cells and a cDNA library is prepared in the pore array sheet. Gel containing a cell lysis reagent (e.g., a surfactant) for lysing cell membrane is placed on the upper portion of the pore array sheet as shown in FIG. 1(a). In FIG. 1, 3 represents sample cells (cell sheet) and 4 represents the gel containing a cell lysis reagent. Then, the upper portion of the cell sheet is brought into contact with a solution containing an electrolyte. The cells may be in direct contact with the electrolyte, or may be in contact with the electrolyte via the gel or the like. In contrast, the lower portion of the cell sheet is also brought into contact with the electrolyte-containing solution through the pores such that an electric field is applied in the vertical direction of the cell sheet. Negatively charged mRNA 5 electrophoretically moves to the lower portion through the pores 6, and is trapped by DNA probe 7 in the pores 6. As shown in FIG. 1(a) by reference numeral 8, after mRNA is trapped in the pores 6, the sample (cell sheet) 3 and the gel sheet 4 were removed. This operation is advantageously performed by using a low melting-point agarose gel, which causes a phase change depending upon temperature, as a gel material, because the agarose gel can be washed out by increasing temperature.

Subsequently, cDNA 9 is synthesized using mRNA 8 trapped by the DNA probe 7 in the pore as a template. This operation is performed by filling the pores 6 with a solution containing a reverse transcriptase and a synthetic substrate and slowly increasing temperature to 50° C. to perform a complementary strand synthesis reaction for about 50 minutes. After completion of the reaction, RNase is supplied through the pores 6 to digest mRNA 8. Then, a solution containing an alkali denaturant and a washing solution are supplied through the pores 6 to remove the residue and degraded products. By the above procedures, a cDNA library as shown in FIG. 1(*b*) reflecting the positions of cells in a tissue sample is constructed within the pore 6.

The number of mRNAs per cell is approximately $10^6$. Assuming that a cell is schematically a round cell having a size of 10 μm in diameter, the number of pores to be used per cell may be about 2500. In other words, if 1000 copies or less of mRNAs are expressed in a cell, a single-copy cDNA can be produced within a pore, in average. If the number of mRNAs is larger than that, a plurality of copies of cDNAs for the same type of mRNA are to be produced per pore. If the size of the pore is reduced, the number of each type of mRNAs can be controlled to be a single copy or less per pore. (Furthermore, if cells are treated one by one to increase the cDNA library preparation region per cell, the number of copies per pore can be reduced to a single copy or less). In each pore, various types of cDNAs (400 cDNAs) are produced in average. By analyzing and determining which pore of the 2500 pores (in average) corresponding to a single cell mRNA is immobilized and reverse-transcribed to cDNA, it is possible to determine mRNA distribution within the cell.

Figure 24:
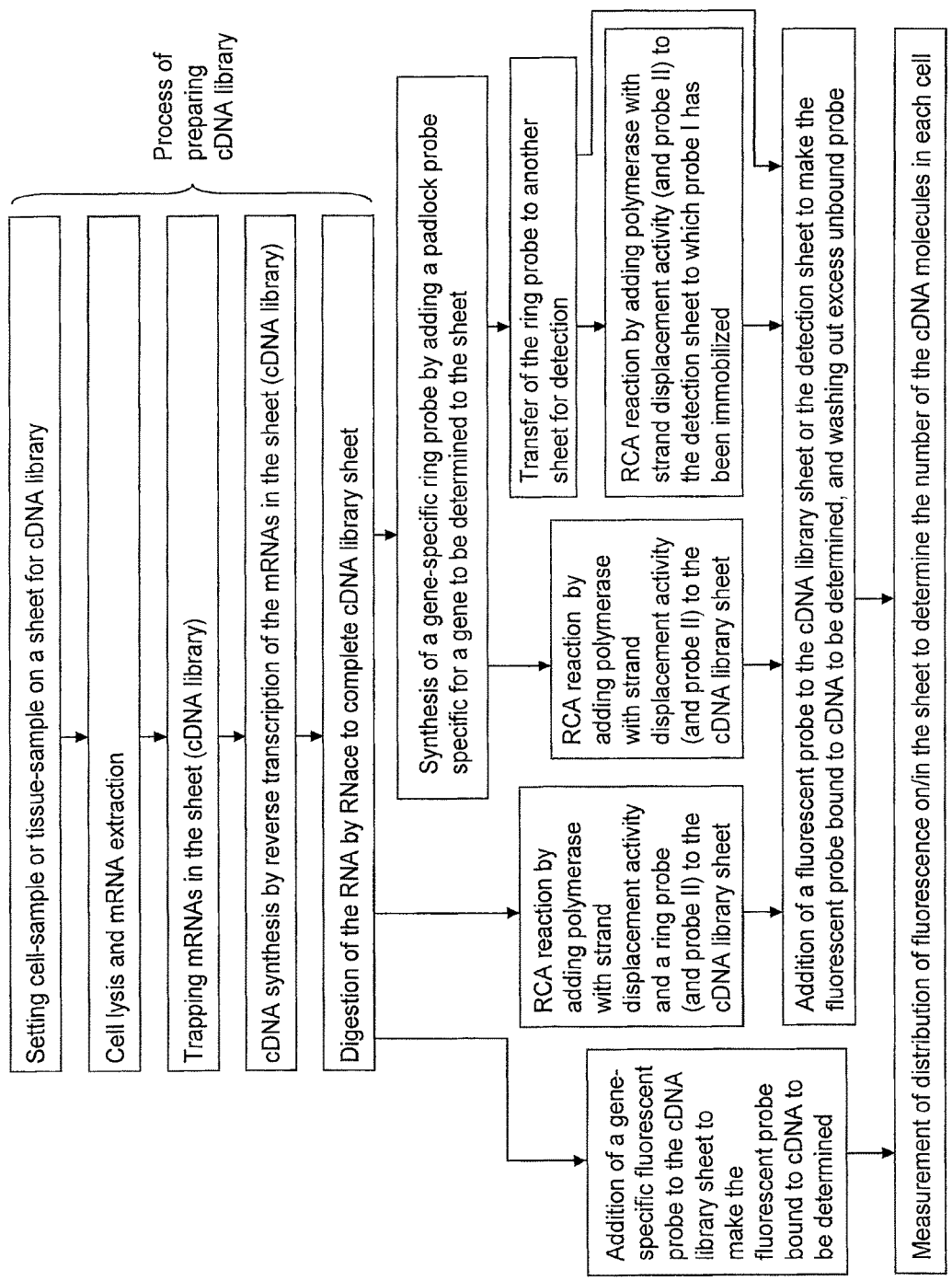
FIG. 24 shows a flowchart in the case of detecting gene expression based on fluorescence.

Subsequently, cDNA 9 produced is measured. For example, probes 10 are prepared for each type of target cDNAs by using rolling circle amplification (RCA) and sequentially supplied to the pore 6. Measurement can be made by fluorescence detection or chemiluminescence detection. In this Example, a case where rolling circle amplification (RCA) and chemiluminescence detection are employed will be described as an example. In other approaches, polymerase chain reaction (PCR), Nucleic Acid Sequence-Based Amplification (NASBA) method, Loop-Mediated Isothermal Amplification (LAMP) method and others can be used as an amplification method. A case using RCA is shown by a flowchart in FIG. 24 and FIG. 25. FIG. 24 shows a case of fluorescence detection and FIG. 25 shows a case of chemiluminescence detection.

As shown in FIG. 24, in a case of detecting fluorescence, after a ring probe is transferred from the cDNA library sheet to another sheet for detection, RCA reaction is performed for detection and quantification. In another method, fluorescence is detected without RCA reaction. Alternatively, a cDNA library sheet is directly used for detection and quantification. Also in this case, there are methods employing and not employing RCA reaction.

Figure 25:
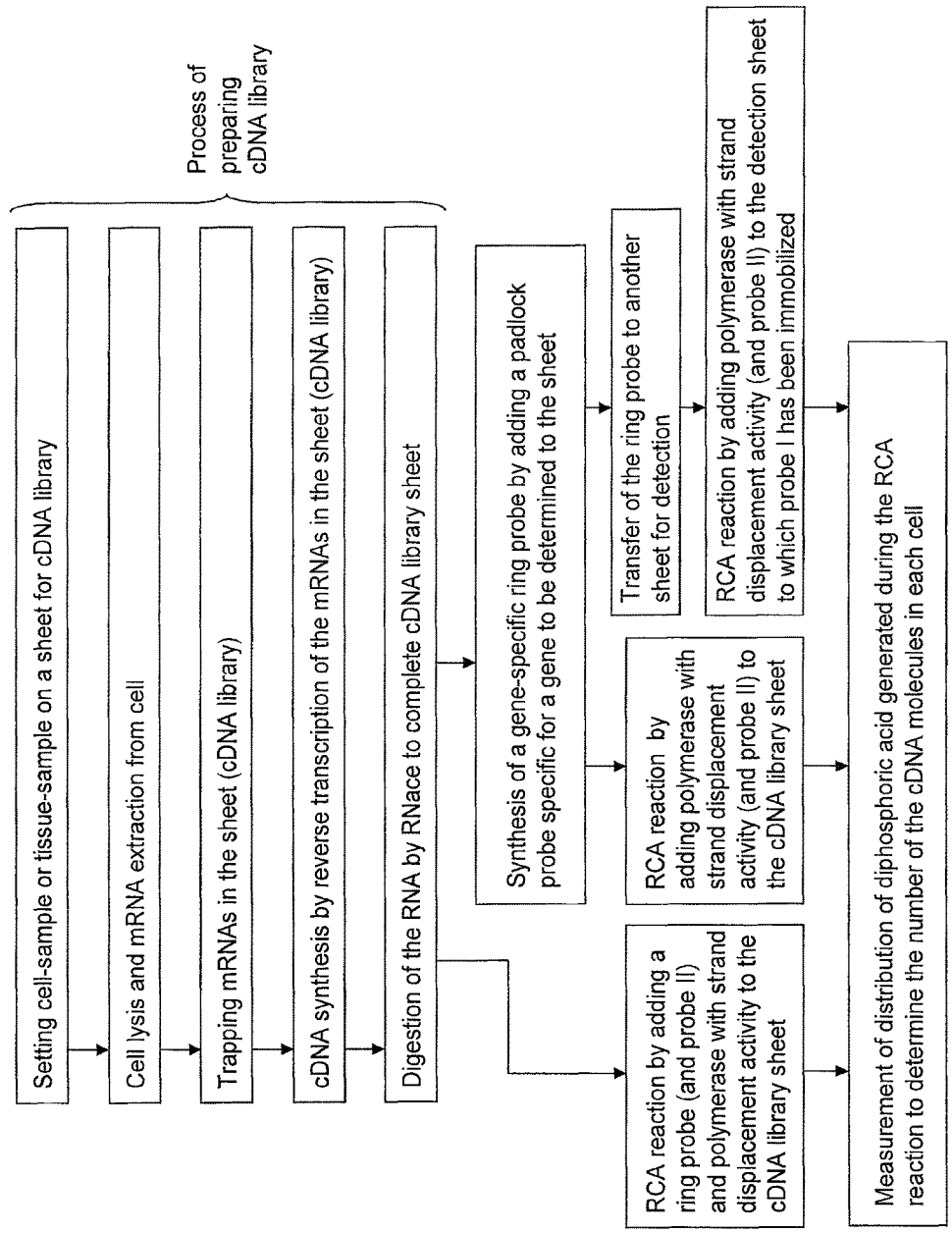
FIG. 25 shows a flowchart in the case of detecting gene expression based on chemiluminescence.

In a case of detecting chemiluminescence, as shown in FIG. 25, after a ring probe is transferred from a cDNA library sheet to a detection sheet and an RCA reaction is performed. Diphosphoric acid generated in the reaction is detected based on chemiluminescence. In another method, an RCA reaction is performed within the cDNA library sheet and the resultant chemiluminescence is measured. More specifically, in this chemiluminescence detection method based on RCA reaction, there are an approach in which a ring probe is formed from a padlock probe by specific ligation and then an RCA reaction is performed, and an approach in which a ring probe is directly and specifically hybridized with cDNA to perform RCA reaction.

A DNA probe capable of hybridizing with both ends of each of cDNAs (target) to form a ring is prepared. In the specification, the DNA probe is referred to as a padlock probe. After a ring is formed, the DNA probe is referred to as a ring probe. In this Example, the probe is designed so as to have 110 bases in length and two common sequences (common sequence I and II) of about 20 bases in the internal regions although the hybridization sequences vary depending upon the gene (target) to be measured. First, a DNA probe 10 corresponding to a first target gene is placed in the pore 6 to hybridize with a target cDNA. A solution contains ligase and the hybridized probe forms a ring (referred to as a ring probe) (see FIG. 1(*c*)). Temperature is increased to inactivate ligase simultaneously with releasing the ring probe from the target cDNA 9. The free ring probe 10 is electrophoretically transferred or by sending solution to another pore array sheet (also referred to as "detection pore array sheet") in which common probe I capable of hybridizing with the common sequence I has been immobilized within a pore, and hybridized with common DNA probe I immobilized in the detection pore array sheet to trap the ring probe 10.

In this Example, after a cDNA library was prepared, a DNA probe (padlock probe) specific to the gene (target) to be measured was used. However, in the case of performing RCA reaction within a cDNA library sheet, the ligation process may be omitted by using a ring form probe from the beginning in place of using a padlock probe and RCA reaction can be performed.

In this Example, a pore array sheet formed of a material obtained through anodic oxidation of Si and capable of absorbing visible light was used as the detection pore array sheet in order to measure individual signals derived from DNAs trapped in pores based on chemiluminescence.

Figure 3:
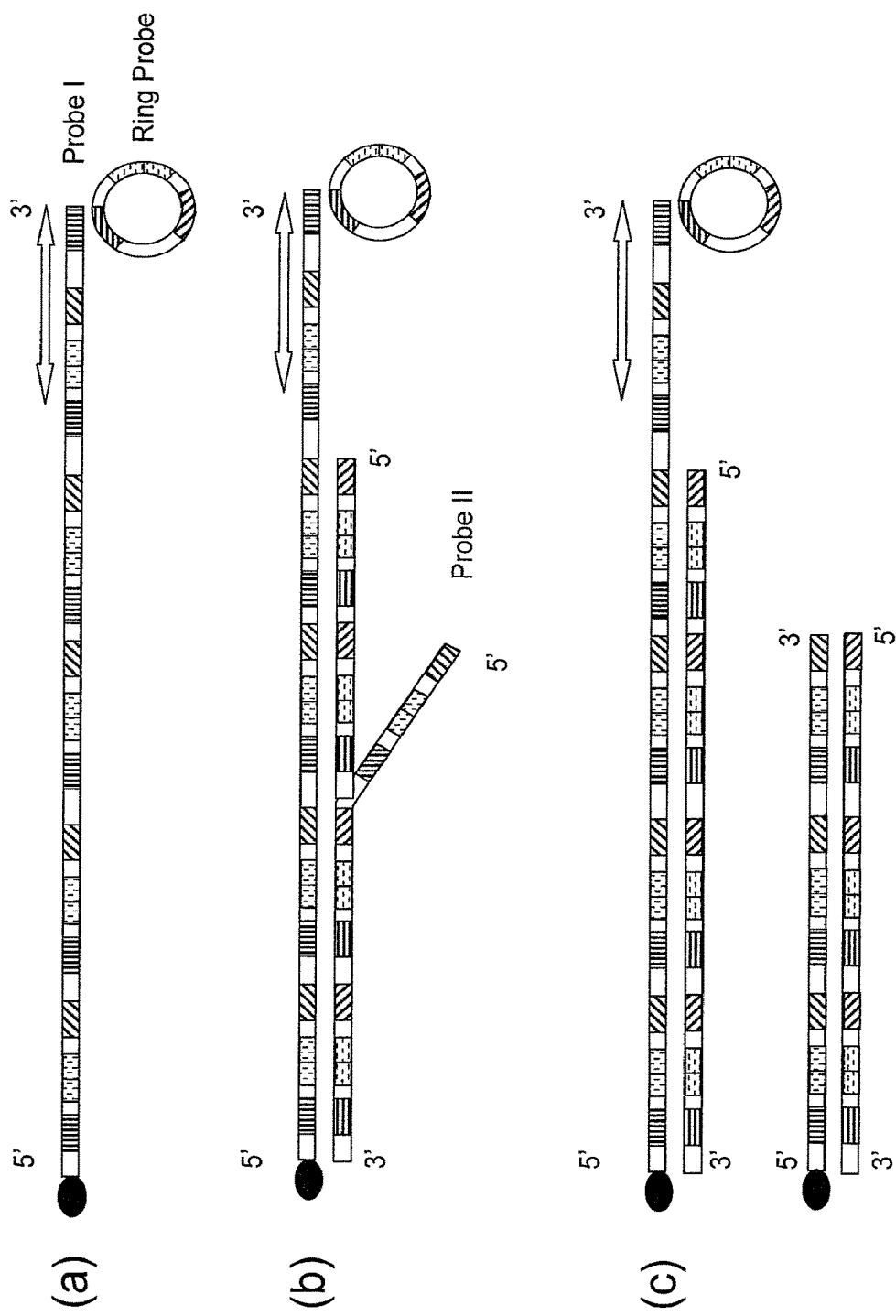
FIG. 3 schematically shows a rolling circle amplification (RCA) reaction.

Next, a reaction solution, which contains common DNA probe II having the same sequence as that of common sequence II, DNA polymerase with strand displacement activity, a DNA synthesis reaction substrate, and a reagent for converting diphosphoric acid to ATP and a reagent for mediating a reaction between ATP and luciferin to provide chemiluminescence, is poured in pores at 4° C. Next, enzymes present except within the pores are washed out and both surface of a sheet is covered with Mebiol Gel (Mebiol Inc.), which is present in the state of a solution at 15° C. or less and turns into non-flowable gel at 25° C. or more. This can suppress background light emission, which is emitted from the portion except the sheet; at the same time, can prevents discharge of the enzyme poured to outer portion of the pores. If the temperature is set at 37° C., which is an optimal temperature for synthesis of a DNA complementary strand, DNA probe I hybridized with a target cDNA starts extension of a DNA complementary strand. Even if the strand extends one round, formation of sequence is repeated by strand displacement activity. FIG. 3(*a*) shows how to amplify two common sequences, I and II, and the region to be hybridized with cDNA, repeatedly. In FIG. 3, the portion indicated by the arrow at the 3' end of the probes is the region to be hybridized with a ring probe. This is a first step of RCA. In the beginning, probe II has no DNA chain to be hybridized, a reaction for extending a DNA complementary strand does not occur. As DNA chain extension of probe I proceeds, a complementary sequence is formed in the complementary strand. Thus Probe II hybridized with this and extension of a complementary strand is started. As shown in FIG. 3(*b*), probe II starts extension from a plurality of sites in the DNA complementary strand initially extended. The strand extended from a probe hybridized with the site relatively close to the 5' end is being removed by a complementary strand which hybridizes with a site close to the 3' end and starts extension. A complementary strand completely removed into a single-strand is trapped by probe I immobilized in the proximity thereof, and probe I is extended to form a double-strand. As a result, the state shown in FIG. 3(c) is achieved. Actually, such processes are repeated in parallel. This is a second step of RCA. In this Example, probe II was supplied in the beginning of the complementary strand synthesis. However, it may be possible that RCA is performed first by use of probe I to form a long DNA strand, and thereafter, the aforementioned reagents are supplied and a complementary strand is synthesized by use of probe II, and subsequently a chemiluminescence reaction is performed.

If the reaction is performed for about 45 minutes, a target sequence consisting of about 110 bases may be amplified about 1000 times. In contrast, with the DNA strand produced with probe I as an initiation point, about 1000 probes II are hybridized and complementary strands are synthesized. The number of DNA copies by these reactions is about 500,000 copies. The sectional view of the sheet in this state is shown in FIG. 1(d). The number of diphosphoric acid molecules produced by the reaction is $10^8$ or more. In the ATP production reaction and the light emitting reaction using the diphosphoric acid molecules, if a substrate is sufficiently present, light emission from $10^8$ photons/second can be achieved. This is the amount that can be sufficiently detected by a cooled CCD camera, etc., even in consideration of light-receiving efficiency and quantum efficiency for detection, etc.

Whereas, to measure fluorescence, a complementary strand is extended by RCA using probe I immobilized within a pore and then, probe II (fluorescent probe) tagged with a fluorescent label is introduced in the pore and hybridized with the RCA product, and fluorescence is measured. The state of the RCA product hybridized with the fluorescent probe is shown in FIG. 1 (e).

Furthermore, in the Example, different sheets, i.e., a detection pore array sheet used for RCA and a cDNA library sheet for preparing cDNA in pores, are used. A ring probe prepared by using the cDNA library sheet is transferred to a pore array sheet for detection (detection pore array sheet) and then RCA was performed. This is, in repeated use of the cDNA library sheet, to prevent the reagents and probes used in a previous measurement from interfering with measurement. All reactions and measurements can also be performed within a pore of the sheet in which a cDNA library is formed.

Next, a method for immobilizing a DNA probe within a pore of the cDNA library sheet will be more specifically described. The surface of a pore within the sheet should be a surface, with which poly-T DNA probes are highly densely immobilized; at the same time, and which does not adsorb nucleic acids such as mRNA and a ring probe, and proteins such as ligase and polymerase. In this Example, a silane coupling agent for immobilizing DNA and a silanated MPC polymer (2-methacryloyloxyethylphosphoryl choline polymer) for preventing adsorption are simultaneously immobilized in an appropriate ratio to a pore surface via a covalent bond to attain highly dense immobilization of DNA and stable suppression of adsorption of nucleic acids and proteins. Actually, first a porous sheet 1 made of alumina was immersed in an ethanol solution for 3 minutes. Then, a UVO3 treatment is applied for 5 minutes to the sheet, which is washed three times with ultrapure water. Next, the sheet was immersed in a 80% ethanol solution containing 3 mg/ml silanated MPC polymer, $MPC_{0.8}$-$MPTMSi_{0.2}$ (MPC: 2-Methacryloyloxyethyl phosphorylcholine/MPTMSi: 3-Methacryloxypropyl trimethoxysilane) (see, Biomaterials 2009, 30, 4930-4938, and Lab Chip 2007, 7, 199-206) having an average molecular weight of 9700 (polymerization degree 40), 0.3 mg/ml silane coupling agent, GTMSi (GTMSi: 3-Glycidoxypropyltrimethoxysilane, Shin-Etsu Chemical Co., Ltd.), and 0.02% acetic acid serving as an acid catalyst for 2 hours. After washed with ethanol, the sheet was dried in a nitrogen atmosphere and heated in an oven at 120° C. for 30 minutes. Next, to immobilize DNA, 500 μL of a solution containing 1 μM poly-T DNA probe (Oligo $(dT)_{30}VN$), 7.5% glycerol and 0.15 M NaCl in 0.05M boric acid buffer (pH8.5) was added dropwise to the sheet and allowed to react in a humidified chamber at 25° C. for 2 hours. Finally, unreacted glycide groups were blocked. To remove excess DNA probes, the sheet was washed with a washing solution containing a sufficient amount of 10 mM Lys, 0.01% SDS and 0.15 M NaCl in boric acid buffer (pH8.5) for 5 minutes. After the washing solution was removed, the sheet was washed with a solution containing 0.01% SDS and 0.3M NaCl in 30 mM sodium citrate buffer (2×SSC, pH7.0) at 60° C. to remove excess DNA. In this manner, immobilization of the DNA probe and surface treatment were completed.

Now, an array of cells will be described as an example. The same will be applied to the case where a tissue section sample is used. A house keeping gene GAPDH (GenBank Accession Number NM_002046) actually measured will be described as an example. A sample containing cells of about 1,000,000 or less was placed in a tube. To this, 1×PBS (500 μL) was added. After the cells were washed by suctioning and discharging the solution so as not to damage the cells, the solution was discarded so as not to leave PBS as much as possible. To this, 1×PBS (50 μL) cooled to 4° C. was added. This sample is aligned on a sheet 1 in the form of array. More specifically, on a sheet having pores of 0.1 μm in size and a thickness of 60 μm, regions of 20 μm in diameter positively charged are provided at the intervals of 30 microns by a surface treatment. Since the surface of cells is negatively charged, when the cells are allowed to flow on the surface of the sheet, the cells are trapped by the sheet surface at intervals of 25 μm. Since the sheet area which is used in trapping is equivalent to a circle having a diameter of 25 mm, about 1,000,000 cells can be trapped. Actually, when cells were allowed to flow and trapped by the sheet, the cells were successfully trapped by about 60% of the cells at a rate of one cell per an appropriate site.

Figure 2:
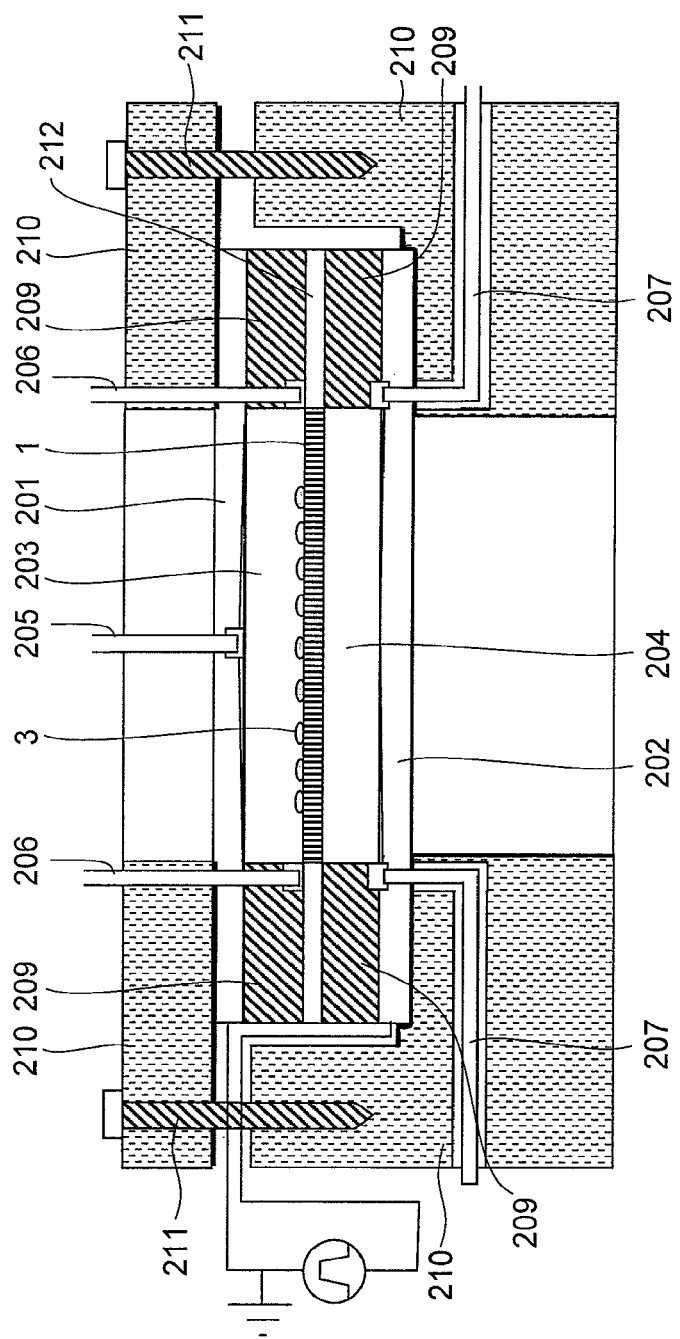
FIG. 2 shows an example of a reaction cell for use in preparing a cDNA library.

FIG. 2 shows an example of a reaction cell used for trapping cells. By use of the reaction cell, cells 3 can be individually immobilized onto the sheet 1 having a diameter of 25 mm and the interior of the pores 6 can be filled with a solution. To fill the periphery of the sheet with the solution, an upper reaction region 203 and a lower reaction region 204 are formed so as to be filled with a reaction solution by providing a protection ring 212 made of polypropylene around the sheet 1, providing a spacer 209 having a thickness of 1 mm on and under the protection ring, and providing a upper cover 201 and a lower cover 202 having electrodes formed by sputtering inside of upper and lower covers so as to sandwich these. To immobilize the spacer 209 and upper and lower covers 201 and 202, an immobilization jig 210 and a screw 211 were used. A buffer solution was injected from an inlet 205 and discharged from an upper outlet 206 and a lower outlet 207 to fill the interior with the solution. Next, from a cell flow channel (inlet 205), cells were fed in the reaction cell while shaking the reaction cell. The cells are trapped by the portion positively charged. Needless to say, the cells may be trapped by a container having a space for housing a single cell. Then, to low melting-point agarose gel (SeaPrep Agarose; gelation temperature:19° C., melting point: 45° C. in a concentration of 2%) which causes phase conversion between a gel state and a liquid state depending upon temperature, a cell lysis reagent is mixed. By using the resultant solution, cell membrane and cell tissue are lysed to extract mRNA in a state where the cells are immobilized at the locations on the sheet.

4% SeaPrep Agarose (Cambrex Bio Science Rockland, Inc.) solution (250 Lysis Solution (495 μL) (TaqMan MicroRNA Cell-to-CT Kit; Applied Biosystems Inc.) and DNase I (5 μL) were mixed well at 40° C. Next, the temperature of the sheet 1 is set at 4° C. After the solution is removed from the reaction regions 203 and 204, the aforementioned cell lysis solution is injected through the inlet 205. After confirming that the solution on the sheet was gelatinized, the temperature of the sheet was raised up to 20° C., a reaction was performed for 8 minutes. Thereafter, Stopping Solution (solution inactivating DNase) (50 μL) was added onto the gel and reacted for 5 minutes, and then, the gel was cooled to 4° C. 0.5 mL of a solution containing 0.03% PEO (polyethylene oxide) having a molecular weight of 600,000, 0.03% PVP (polyvinyl pyrrolidone) having a molecular weight of 1,000,000 and 0.1% Tween 20 in 10 mM Tris buffer (pH8.0) was added. At this time, the distance between the upper electrode 201 and the lower electrode 202 is set to be 2 mm and the spaces (reaction regions 203, 204) above and below the sheet are completely filled with the aforementioned Tris buffer. While keeping the temperature of the sheet and solution at 4° C., a voltage of +0.8V is applied for 2 minutes with the upper electrode 201 used as a cathode (GND) and the lower electrode 202 used as an anode to electrophorese mRNA negatively charged from the interior of the cells toward the reaction region 204.

In this process, most of mRNAs are trapped by the Oligo dT DNA probes immobilized in pores of the sheet. However, a part of the mRNAs is not trapped by the two-dimensional structure and moves into the buffer (204) under the sheet. To trap mRNAs completely by the Oligo dT DNA probes, the temperatures of the sheet 1 and the solution were raised up to 70° C. and kept for 5 minutes and thereafter cooled at a rate of −0.1° C./sec to 4° C. while reversing the polarity of the voltage to be applied to the lower electrode 202 at every one minute (in the beginning, a voltage of −0.8V was applied for one minute and thereafter +0.8V→−0.8V was applied for one minute. This operation was repeated 10 times). Next, while the solution in the region 203 above the sheet 1 was exchanged by introducing the aforementioned tris buffer from the inlet 205 and discharging it from the outlet 206; the temperatures of the solution and the sheet 1 were raised up to 35° C. to melt agarose gel and unnecessary cell tissues and agarose were washed out. Furthermore, 585 μL of a solution containing 0.1% Tween 20 in 10 mM Tris buffer (pH=8.0), 40 μL of 10 mM dNTP, 225 μL of 5× RT buffer (SUPERSCRIPT III Cell Direct cDNA Synthesis System), 40 μL of 0.1M DTT, 40 μL of RNase OUT (SUPERSCRIPT III Cell Direct cDNA Synthesis System) and 40 μL of Superscript III (reverse transcriptase: SUPERSCRIPT III Cell Direct cDNA Synthesis System) were mixed. Immediately upon discharging the solution soaking the sheet 1 from the outlets 206 and 207, the solution containing reverse transcriptase prepared above was injected through the inlet 205. Thereafter, the temperatures of the solution and the sheet 1 were raised to 50° C. and kept for 50 minutes to complete the reverse transcription reaction. Thereafter, the temperature was kept at 85° C. for 1.5 minutes to inactivate the reverse transcriptase and then reduced to 4° C. Thereafter, 10 mL of a solution containing 0.1% Tween 20 containing RNase in 10 mM Tris buffer (pH=8.0) was injected from the inlet 205 and discharged from the outlets 206 and 207 to degrade RNA. The same amount of alkali denaturant was injected and discharged in the same manner to wash out the residue and degraded products in the pores, and a cDNA library was constructed.

In the Example, the cDNA library is prepared by using about 10,000 pores per cell. The total surface area of the pores per cell is about 0.7 mm$^2$. Since DNA probes are immobilized in a ratio of one or more per area of 100 nm$^2$, the total number of probes is about 7×10$^9$. This is a sufficient amount for trapping mRNAs (total number: about 10$^6$) in a single cell. Since the nucleic acids easily adsorb to the surface of a pore, the pore surface is coated with MCP polymer as a surface coating agent to prevent adsorption, as mentioned above.

By the operation described above, a cDNA library was obtained in which cDNAs derived from a single cell are immobilized on the surface of a number of pores. This should be referred to as a single-cell cDNA library sheet and fundamentally differs from an averaged cDNA library obtained from a number of cells.

From the cDNA library sheet thus obtained, the expression level of each of the various genes is quantitatively determined. Since 10,000 pores are present per cell, the number of cDNAs per cell may be 100 in average. If the number of copies of single-type cDNA per cell is 10,000 or less, an average number of cDNA per pore is one or less. To detect this, a probe capable of hybridizing specifically with each type of cDNA probe is to be used.

As the detection method, methods using chemiluminescence or fluorescence are known. In this Example, a method of using chemiluminescence will be described. As a method of amplifying a target sequence portion of a target cDNA, for example, a polymerase chain reaction (PCR) or a rolling circle amplification (RCA) reaction is known. In this Example, the rolling circle amplification was used since it has a stable amplification rate. An example of the target sequence was shown in FIG. 4 (SEQ ID NO: 1). The DNA probe (padlock probe) capable of hybridizing with the target sequence was shown in FIG. 5 (SEQ ID NO: 2). The padlock probe contains specific sequence portions, which hybridize with a target, and two common sequence portions each consisting of about 22 bases. In this Example, the length was set at 110 bases. The DNA probe is designed such that both ends thereof hybridize with a target and are joined with the help of a repair enzyme, ligase, to form a ring-form DNA (ring probe). The DNA probe (padlock probe) is injected in pores and hybridized with a target to obtain a ring-form DNA (ring probe) through ligation.

More specifically, 10 μL of 2 μM padlock probe, 100 μL of 10× Ampligase buffer (Ampligase DNA Ligase Kits; EPICENTRE Biotechnologies), 100 μL of Ampligase (Ampligase DNA Ligase Kits; EPICENTRE Biotechnologies), 250 μL of BSA (10 mg/mL) and 540 μL of pure water (DW) were mixed. The resultant solution was injected through the inlet and reacted for 12 hours while keeping at 50° C. Thereafter, the temperature was raised to 80° C. and kept for 20 minutes to inactivate the ligase.

Next, a ring probe is transferred to the detection pore array sheet and measurement is performed. In the pore, common DNA probe I (FIG. 6; SEQ ID NO: 3), which hybridizes with the sequence, of common portion I of a ring probe, is immobilized within the pore and traps the ring probe within the pore. Subsequently, another probe, i.e., common DNA probe II (FIG. 7; SEQ ID NO: 4) having the same 22-base sequence as another common portion II in the ring probe and a polymerase with strand displacement activity were introduced into the pore and an RCA reaction was performed at 37° C. for 45 minutes.

Figure 8:
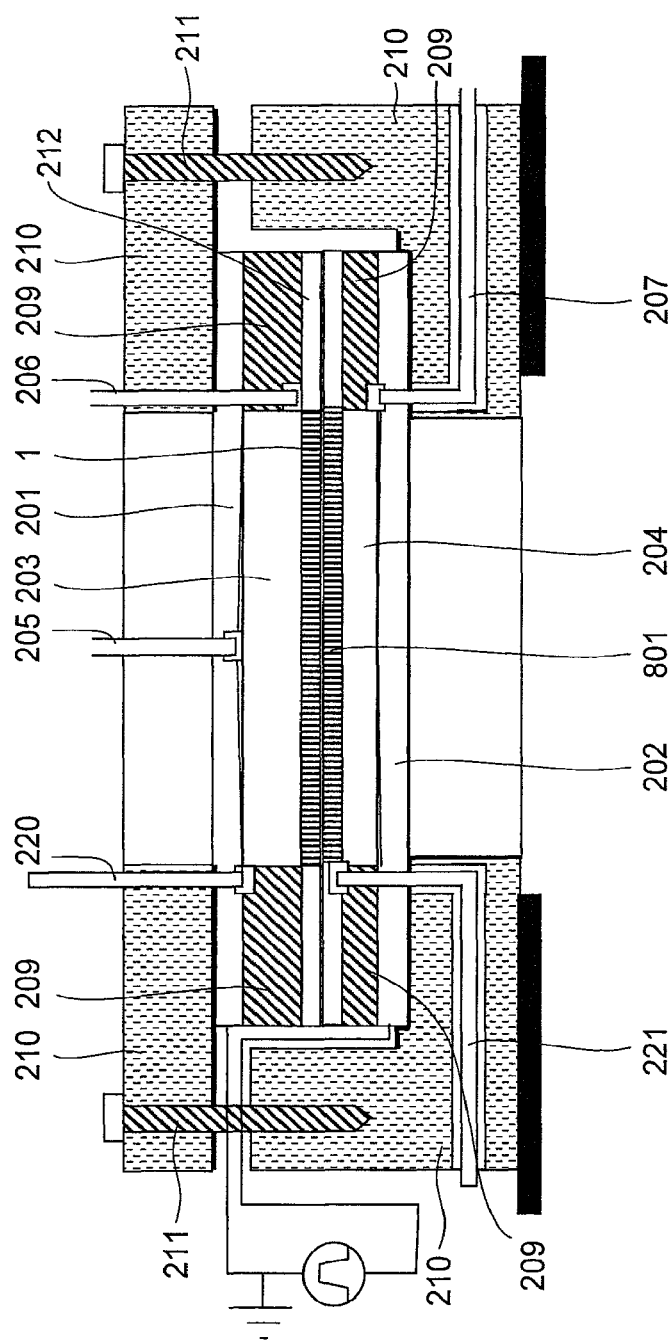
FIG. 8 shows an example of a reaction cell used for measuring chemiluminescence.

To perform the measurement using RCA and chemiluminescence, poly-T probes were immobilized within an opaque sheet obtained by anodic oxidation of Si and coating with an MPC polymer was performed in the same manner. Similarly to the case of the alumina sheet, the sheet was set to have a pore of 0.1 μm in diameter and a diameter of 25 mm and a thickness of 100 μm. As shown in FIG. 8, under the sheet 1 having ring probes formed thereon, a sheet 801 having probes I immobilized thereon was arranged so as to overlay to assemble a reaction cell. While a voltage of +0.4V was applied to the electrode provided inside the lower cover 202, heating was performed at 95° C. for one minute, cooling was performed at a rate of 1° C./sec to 65° C. and the temperature was kept for 10 minutes. Application of voltage was terminated, and the temperature was cooled to room temperature. The cDNA library sheet made of alumina was removed while leaving the sheet 801 having probes I hybridizing with ring probes alone. In this manner, a reaction cell was again assembled.

100 μL of 10× φ29 luminescent reagent buffer (0.5 M Tricine, 0.1 M MgAc, 0.1M $(NH_4)_2SO_4$, 4 mM DTT, 4 mM D-Luciferin, 0.02 mM APS), 10 μL of free DNA probe II (0.1 μM), 50 μL of 10 mM dNTP, 25 μL of 10 mg/mL BSA, 50 μL of 10 U/μL φ29 polymerase (New England Bio Labs), 100 μL of thermostable luciferase (4258.1 GLU/mL; Kikkoman) and 50 μL of ATP Sulfurylase (30 U/mL; New England BioLabs) were mixed with 625 μL of pure water (D.W.) and the resultant mixture was injected through the inlet 205. Immediately upon injection, excess reagents are removed through outlets 206 and 207 such that no pressure difference is produced between above and below the sheet. Next, a solution mixture of a 10× φ29 luminescent reagent buffer and Mebiol Gel cooled to 4° C. in a blending ratio of 1:9 is injected gently through outlets 220 and 221 so as not to produce pressure difference. Since the reaction cell is kept at 37° C., Mebiol Gel is immediately gelatinized. Thereafter, an RCA reaction was performed for 20 minutes.

Figure 9:
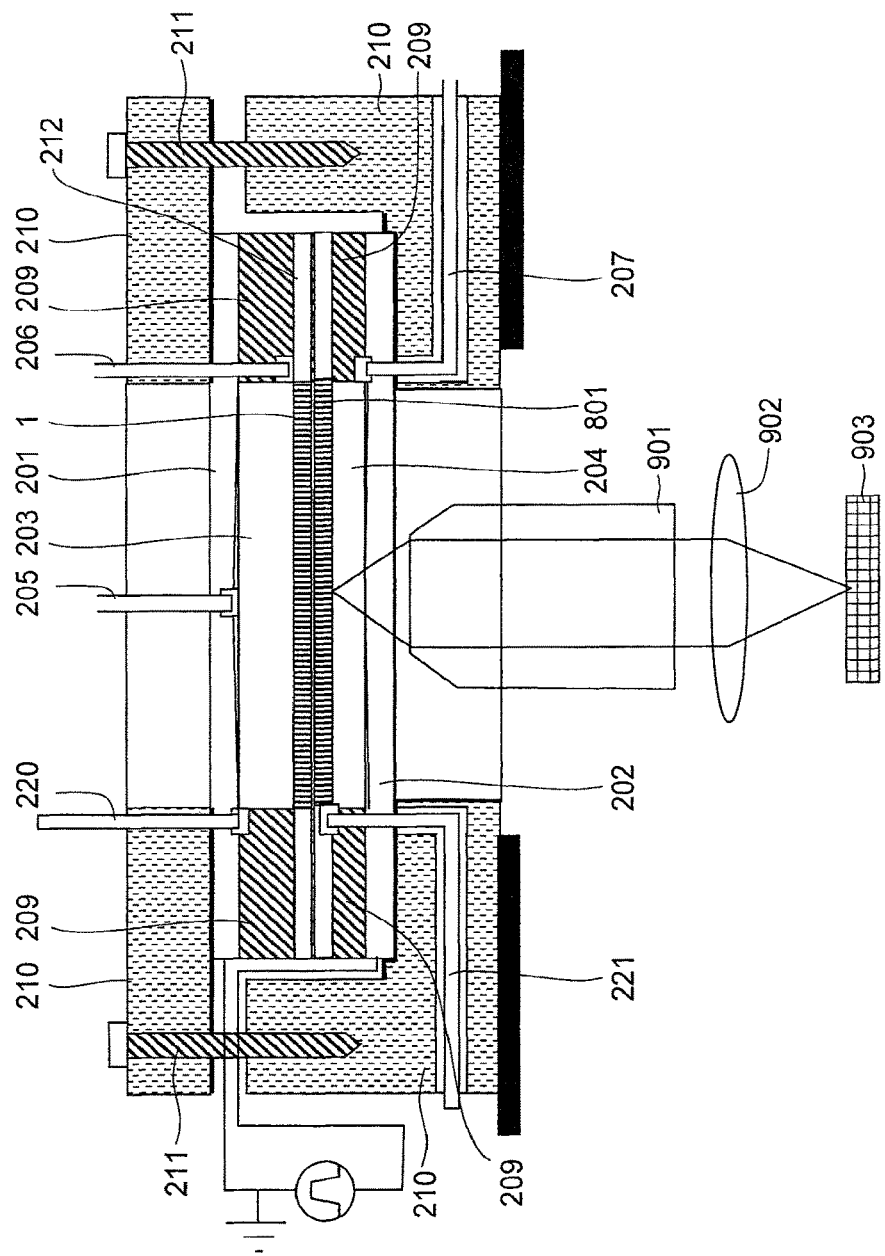
FIG. 9 shows an example of an optical system used for measuring chemiluminescence.

Next, in the optical system shown in FIG. 9, chemiluminescence is continuously measured. In the Example, an objective lens 901 having NA of 0.8 and a working distance of 3.3 mm, an imaging lens 902 and a cooled CCD camera 903 (1000×1000 pixels, a pixel size of 13×13 μm, a quantum efficiency of 0.9) were used. The magnification of the optical system was set at 50× and a luminescence image was obtained by focusing on the lower surface (sheet 801 close to the lower cover 202) of the sheet. Here, another image pickup device such as a CMOS image sensor may be used. The resolution in this case was 0.5 μm, which was almost a marginal resolution. A single frame had a size of 0.26 mm squares and the exposure time was set to be 3 seconds. Measurement was performed by dividing a measurement region of 25 mm in diameter into 7500 regions. From 7500 chemiluminescence images, chemiluminescent spots are extracted and mapped on the measurement region. The positions of cells on the sheet were also obtained from a bright-field image and compared with the positions of chemiluminescent spots. In this manner, the number of GAPDH molecules expressed was successfully confirmed in individual cells. The sheet prepared herein can be repeatedly used. A padlock probe specific to a gene (target) whose expression level is desired to know is prepared, the process after the ligation reaction is repeated in the same manner as mentioned above, and thus, the expression level of a target gene per cell can be highly accurately determined by counting luminescent spots. Even if the amplification efficiency of an RCA reaction changes and timing of measurement is changed in the middle after the RCA reaction starts, since the presence or absence of chemiluminescent spots is determined in the same screen, no problems occur. The number of chemiluminescent spots directly corresponds to the number of mRNA molecules and its quantitative error can be suppressed to the measurement error according to the Poisson distribution.

In this Example, using a padlock probe (SEQ ID NO: 2), which specifically hybridizes with GAPDH (GenBank Accession Number NM_002046), a sequence-specific RCA reaction was performed, and thereafter, quantification was made by counting chemiluminescent spots. However, since cDNA is kept in the original state, it is possible that, after GAPDH is quantitatively evaluated, other gene-specific probe is introduced and subjected to the same operation to determine a gene expression distribution for the other gene, thereby analyzing a gene expression profile. In other words, the cDNA library can be repeatedly used to determine highly accurate expression distribution of desired all types of genes.

Figure 10:
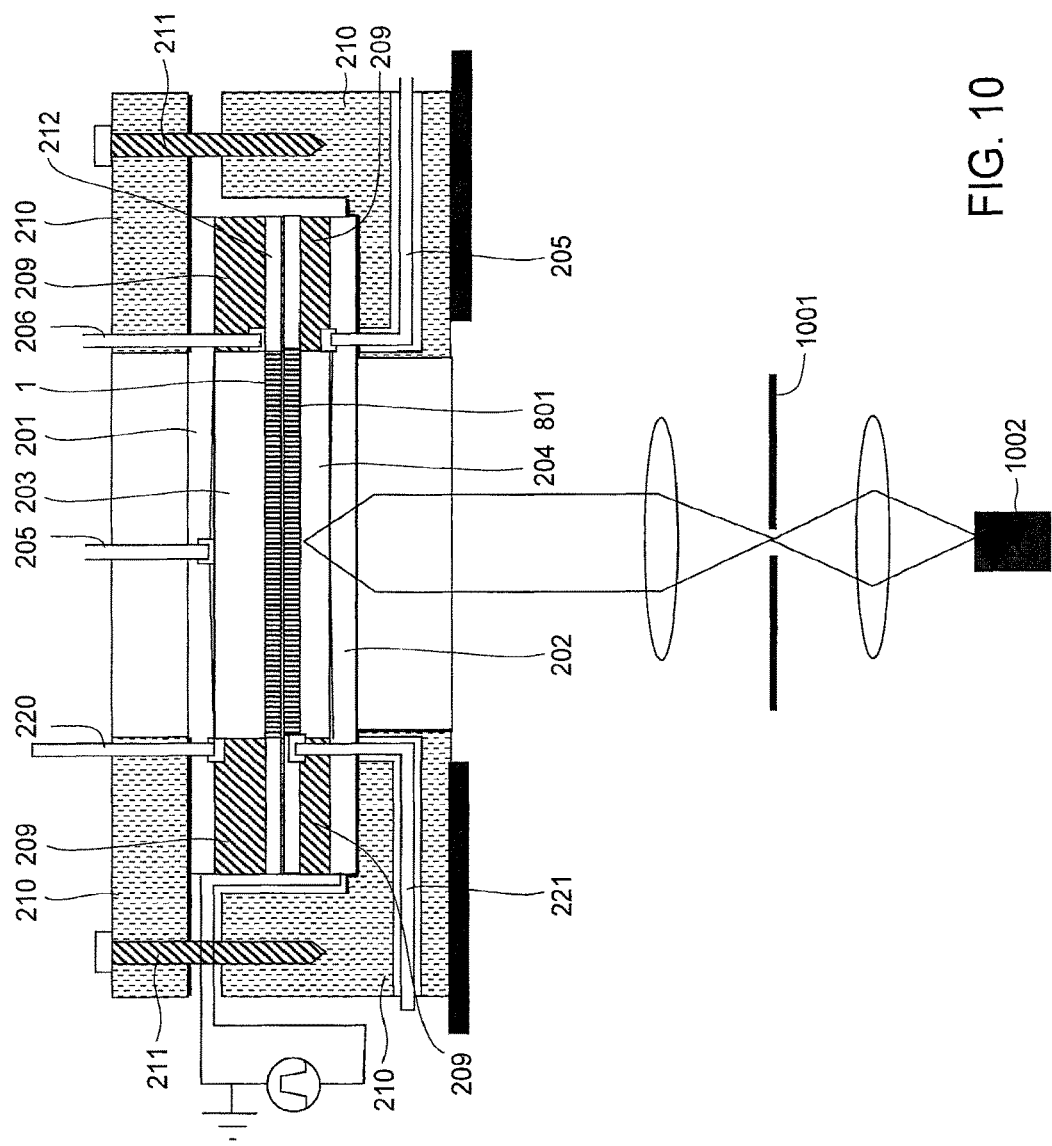
FIG. 10 shows an example of a confocal optical system used for measuring chemiluminescence.

In this Example, in order to suppress background light emission from regions except within the sheet, Mebiol Gel was used to eliminate enzymes present in the regions except within the sheet. However, if the number of cells is low and the measurement area is narrow, the effect of the background may be suppressed by using a confocal optical system as shown in FIG. 10 in place of using Mebiol Gel. In FIG. 10, 1001 represents a slit, which can suppress the depth of field in the z direction within 0.01 μm or less. As a device 1002, either an avalanche photodiode (APD) or a photomultiplier tube (PMT) may be used.

In another embodiment, in the same optical system as shown in FIG. 8, an enzyme (luciferase and ATP-sulfurylase) required for chemiluminescence may be immobilized onto the surface of the sheet and Mebiol Gel may not be used. A number of methods are known for immobilizing an enzyme; however, in this Example, in immobilizing probe I, streptavidin is simultaneously mixed with probe I and reacted with it. An amino group on the surface of streptavidin reacts with a silane coupling agent to immobilize streptavidin. In this state, biotinylated luciferase and biotinylated ATP-sulfurylase are mixed and allowed to react for 30 minutes at room temperature to complete immobilization of luciferase and ATP-sulfurylase to the surface. Thereafter, a step of injecting Mebiol Gel is omitted, and an RCA reaction and chemiluminescence measurement are performed. In this manner, chemiluminescence measurement can be performed in the same manner as mentioned above. Measurement may be performed based on fluorescence and the details thereof will be described in Example 2.

Furthermore, in place of a sheet obtained by anodic oxidation of aluminum and silicon, a capillary plate prepared by bundling capillary tubes, extending and slicing the bundle may be used for carrying out exactly the same method. However, since the diameter of pores of a commercially available capillary plate is 1 μm in minimum, the resolution becomes 1/10. In counting the number of mRNA molecules, the maximum measurable number of molecules per cell becomes 100. In such a case, the range of quantitative analysis can be widened by changing the amount (intensity) of chemiluminescence stepwise. The most suitable method using a capillary plate will be shown below. In the capillary plate used in the case, the pore diameter was 6 μm; the diameter of the region in which pores were formed was 20 mm and the outer diameter was 25 mm; and the thickness was 1.0 mm (manufactured by Hamamatsu Photonics K. K.). To the inner wall of the pores, a silane coupling treatment was applied simultaneously with an anti-adsorption surface treatment and oligo DNA containing a poly T sequence was immobilized onto the inner wall of the pores to prepare a cDNA library sheet in the same manner as in the case of a membrane. At this time, since the diameter of pores formed in the capillary plate is large, in order to mitigate a reduction of resolution, oligo DNA containing a poly-T sequence was immobilized on magnetic beads coated with streptavidin and having a diameter of 1 μm within the capillary plate and the resultant beads are packed in pores of the capillary plate and used in trapping cDNA. In the same manner, a cDNA library could be prepared.

Example 2

Figure 11:
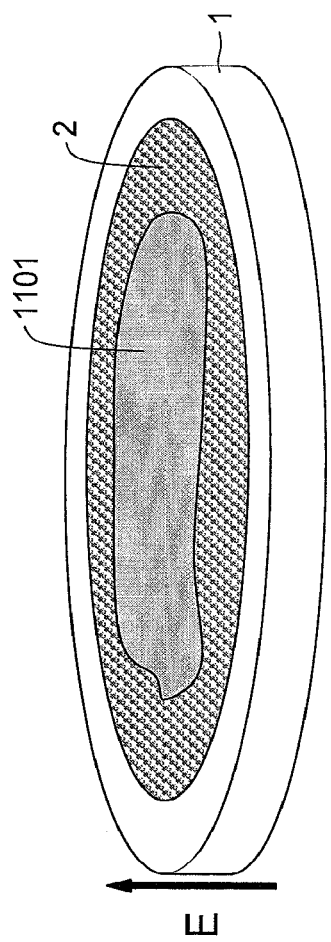
FIG. 11 shows an example of a method for preparing a cDNA library from a tissue section sample.

This Example is outlined in FIG. 11. This is an example of using a two-dimensional cDNA library sheet, which was constructed from a tissue slice sample 1101 in a pore array sheet. A frozen tissue slice was cut by a microtome into a film-form sample having a thickness of about 5 to 20 μm. As shown in FIG. 11, the tissue slice sample 1101 is mounted on a pore array sheet 1 made of alumina and immediately covered with a low melting-point agarose containing a cell lysis reagent. The agarose solution remains in a state of solution at 35° C. The sheet 1 is immediately gelatinized by cooling it to 4° C. Thereafter, the sheet is set in the reaction cell shown in FIG. 2, and mRNA is extracted in the same manner as Example 1.

A solution, which is prepared by mixing a low melting-point agarose gel (SeaPrep Agarose; gelatinization temperature is 19° C., melting point is 45° C. at an agarose concentration of 2%) and a cell lysis reagent, is used to lyse cell membrane and cell tissue while the positions of cells are fixed in sheet-form cell slice sample to extract mRNA. Chemiluminescence can be measured; however, in this Example, how to measure fluorescence will be more specifically described.

After mRNA is immobilized within the sheet, a repeatedly usable cDNA library sheet is prepared in the same manner as in Example 1. Thereafter, cDNA within the sheet is labeled with a gene(target)-specific fluorescent probe, washed and then fluorescence can be directly measured. Alternatively, after an amplified product, which is obtained by a chemical amplification method such as RCA and PCR, is hybridized with a fluorescent probe, fluorescence may be measured. Furthermore, a ring probe is transferred (transcribed) to another sheet and then fluorescence may be measured, as shown in Example 1. Moreover, after chemical amplification is performed, fluorescence may be measured. In the Example, a gene-specific padlock probe is introduced from a cDNA library, and a ring probe is transferred to another sheet and amplified by RCA and then fluorescence is measured. This will be more specifically described as an example.

Figure 12:
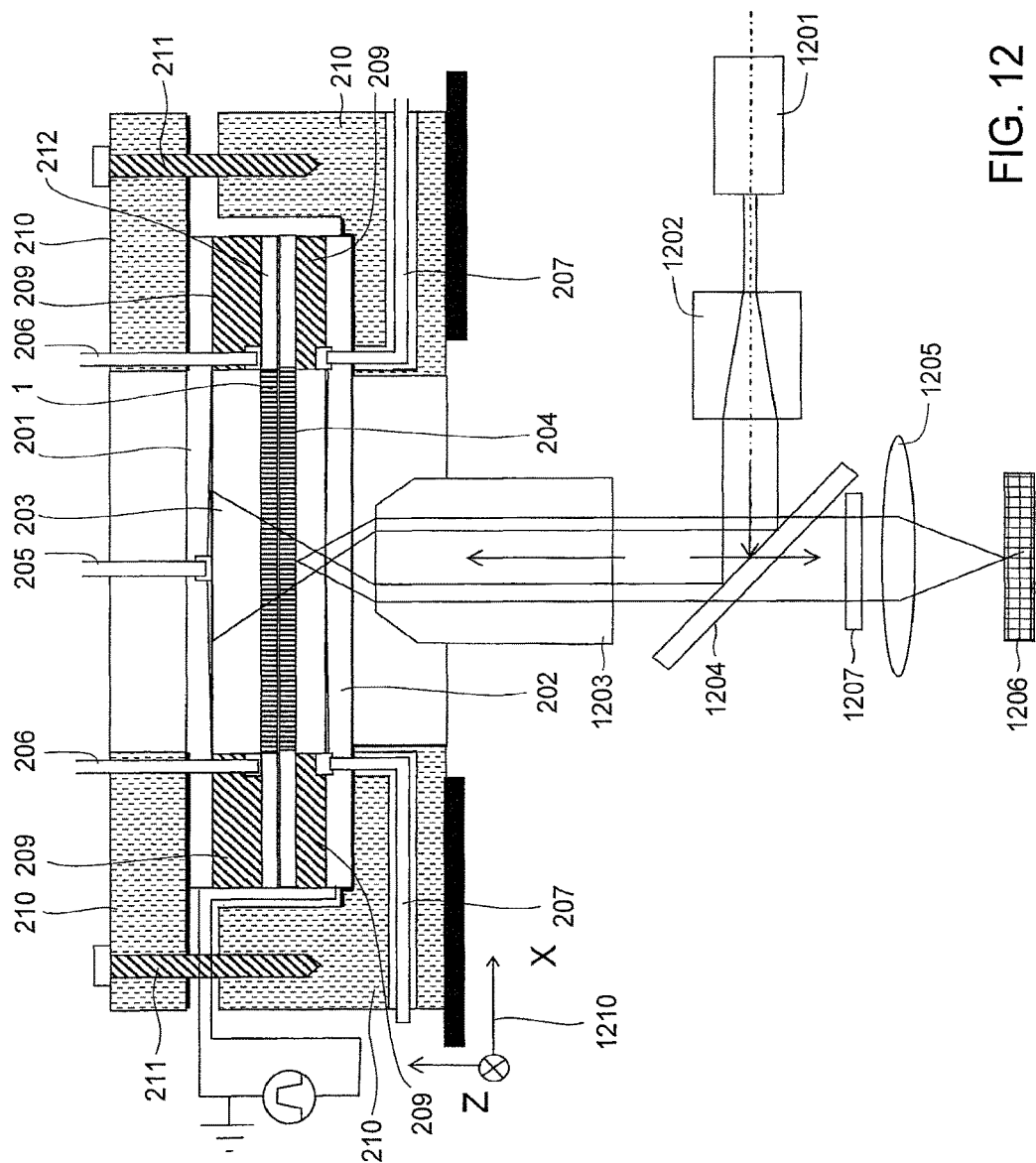
FIG. 12 shows an example of an optical system used for measuring fluorescence.

More specifically, within a cDNA library sheet, ligation is performed in a gene specific manner to prepare a ring probe from a padlock probe. Next, the ring probe is electrophoretically transferred to another sheet. In the Example, as a second pore array sheet for fluorescence measurement, a transparent sheet made of alumina was used. Since the sensitivity of fluorescence measurement is generally high, probe II is not used during an RCA reaction. After the RCA, the same sequence as that of probe II labeled with fluorescence is introduced into pores, in short, a fluorescent probe is introduced. In this manner, a fluorescent image is obtained by the optical system as shown in FIG. 12. Using this image, fluorescent spots are counted to obtain the number of mRNA molecules. In the figure, 1201 represents laser. Since Cy3 was employed herein as a fluorophore, the excitation wavelength of laser was set to be 532 nm and the output level was set to be 20 mW.

Furthermore, the number of mRNA molecules was successfully obtained by using an intercalator (SYTOX Green or POPO 3), which emits fluorescence by binding double-stranded DNAs, in place of probe II labeled with a fluorophore.

The laser outputs a collimated beam having a diameter of 1 mm. This was magnified 5× by a laser beam expander 1202. 1203 represents an objective lens having a NA of 0.8, a working distance of 3.6 mm and a focal distance of 3.6 mm. A fluorescent image was obtained by a cooled CCD camera 1206 at a magnification of 50× by focusing on the lowermost surface of the sheet. In the figure, 1204 represents a dichroic mirror; 1205 represents an imaging lens; and 1207 represents a band pass filter for cutting excitation light. The size of an image in one frame was 0.26 mm squares; the exposure time was 10 msec; and the entire lowermost surface of the sheet was scanned for 70 seconds. Next, the objective lens is moved in the z direction by 1 μm to bring the interior of the sheet into a focus, and scanning was performed in the same manner. It took 80 minutes to obtain an entire sheet image. Since an in-plane resolution was 0.5 μm, the maximum number of mRNA molecules countable per cell of 10 μm in diameter was about 20,000. In addition, the mRNA distribution within a cell was obtained with a resolution of 0.5 μm.

The refractive index of the material of the alumina sheet is as large as 1.76 and the light is scattered relatively significantly due to polycrystalline. For this reason, an RCA reaction is not sufficiently or efficiently occurred. In the case where the number of RCA product having a small number of fluorophores attached per molecule is counted based on fluorescence, fluorescence was sometimes not detected as a fluorescent spot. Therefore, not a focal-point position of the objective lens in the z direction but an RCA product attached with a fluorophore is moved to the lower surface of the sheet and then the lowermost surface of the sheet is brought into a focus to take an image. In this way, a fluorescent image of the entire sheet can be obtained by moving the stage only in the xy direction. An RCA product may be moved by raising the temperature to about 80° C. and applying a voltage of about +0.4V to an electrode on the side of the lower cover. However, in the Example, a voltage of −0.4V is applied to the same electrode to produce a pressure flow from up to down at a rate of 10 μm per second. By virtue of moving the RCA product to the proximity of the lowermost surface of the sheet, a fluorescent image was taken.

Figure 26:
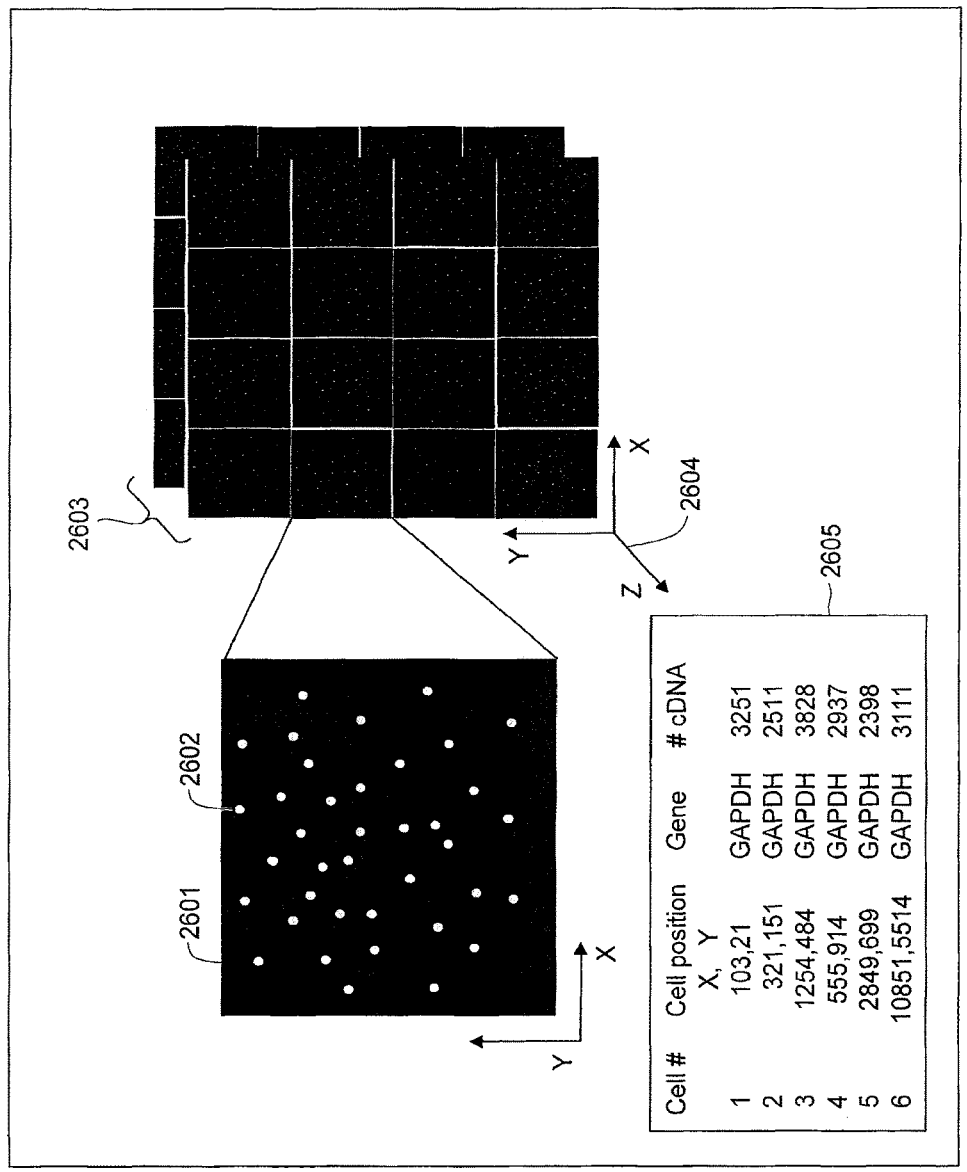
FIG. 26 shows an example of a fluorescent image in the case of fluorescent measurement and an example of the data obtained.

FIG. 26 shows an example of a fluorescent image and data obtained herein. 2601 represents a one-shot image taken by a CCD camera. In the figure, white spots 2602 correspond to fluorescent spots derived from DNA molecules bound with a fluorescent probe after an RCA reaction. The individual spots correspond to mRNA molecules in a cell. The number of mRNA molecules corresponding to specific genes can be obtained by counting the fluorescent spots. Such an image is taken at a plurality of sites (2603) through scanning in the XYZ direction (2604). The XYZ direction coincides with the XYZ direction represented by 1210 in FIG. 12. The fluorescent spots counted are each expressed in the XYZ coordinate. The Z direction is a direction along which an RCA product is electrophoretically moved. Therefore, the Z coordinate is ignored in mapping cell positions on the cDNA library sheet. From which cell mRNA is derived is determined by comparing with microscopic images previously obtained. By mapping data in this manner, a set of data shown in Table (represented by 2605) can be obtained.

Figure 13:
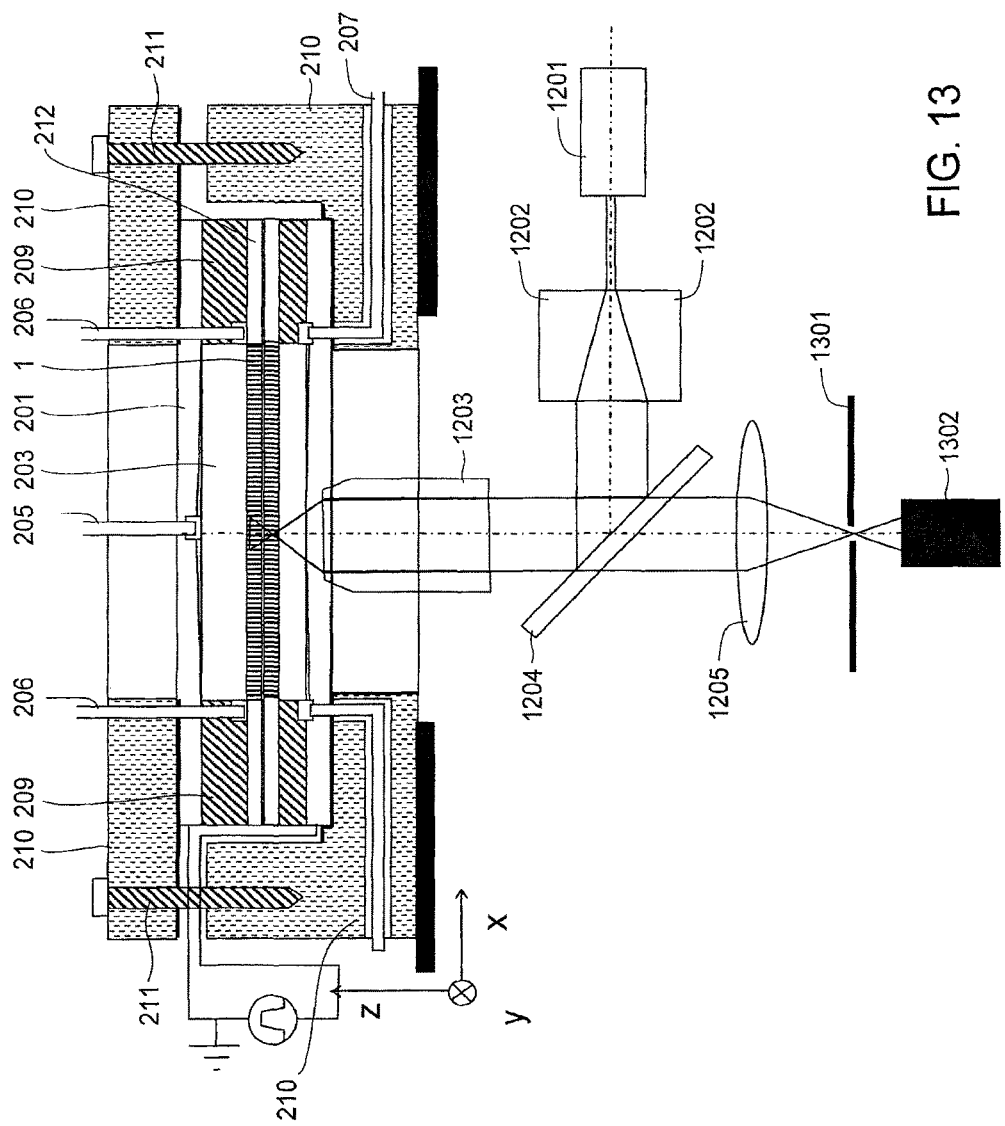
FIG. 13 shows another example of an optical system used for measuring fluorescence.

Next, in the case where the expression distribution within a cell are to be determined by improving the resolution of fluorescent spots, the optical system shown in FIG. 13 may be used. The light emitted from a laser is magnified by a laser beam expander 1202 from 1 mm up to 5 mm and a laser spot was narrowed by an objective lens 1203 having a NA of 0.9, a working distance of 1 mm and a focal distance of 3.6 mm, up to about 1 μm within the sheet. Fluorescence emitted from a fluorophore (Cy3) within a pore in the sheet was collected by the same objective lens 1203, and passed through a dichroic mirror 1204 to cut excitation light, an image was formed by an imaging lens 1205, and at an image forming surface, the confocal optical system was constituted through a pin hole 1301 of 50 μm in diameter. As the light detector 1302, a photomultiplier tube was used; however, APD can also be used. In this case, the resolution of the optical system in the z-direction was 5 nm; however, since 10 nm-pitch z-direction driving mechanism was used, the total resolution in measurement was 10 nm. Since the resolution of the optical system in the XY direction was 0.4 μm, provided that a 60-μm thick alumina sheet was used and the level of maximum expression in a cell is 10000, the gene expression level was determined virtually at the resolution of the optical system. Also in this case, the mRNA distribution within and without the nucleus in a cell can be obtained.

In the description hereinabove, fluorescent was measured by performing RCA reaction in the same sheet as the cDNA library prepared in a pore array sheet, and hybridizing with a fluorescent probe within the sheet, or by electrophoretically transferring a ring probe to a detection sheet and amplifying it by RCA reaction and hybridizing with a fluorescent probe. Fluorescence can be measured not by transferring a ring probe to a detection sheet but by transferring a ring probe to a gel film. Next, this case will be described.

Figure 14:
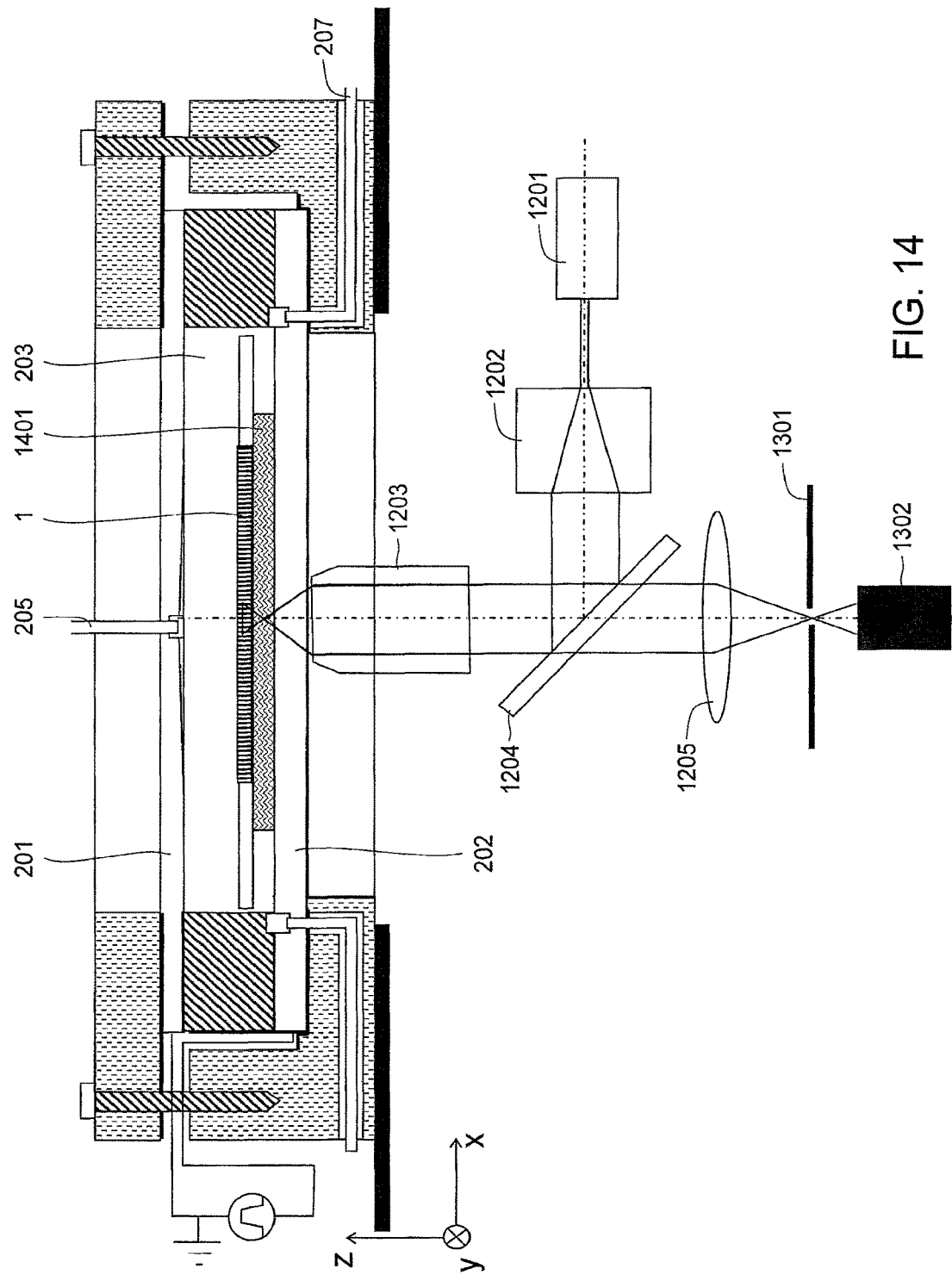
FIG. 14 shows an example of a reaction cell and an optical system used for measuring fluorescence.

A cDNA library is prepared in a pore array sheet. After completion of a cDNA library sheet, a film-form gel 1401 is formed on the lower cover 202 as shown in FIG. 14. On the gel, cDNA library sheet 1 having pores is allowed to adhere to prepare a reaction cell. Next, within the cDNA library sheet, a ring probe is formed sequence-specifically from a padlock probe and electrophoretically transferred to the gel film. The ring probe thus transferred is trapped with common probe I. After a fluorescent probe having a sequence capable of hybridizing with the ring probe is injected, the ring probe is electrophoretically moved to the gel film. In this manner, preparation for fluorescence measurement may be completed or a fluorescent probe may be attached in the same manner after the RCA reaction. This case will be more specifically described below. As the gel to be used herein, any gel material can be used. Examples thereof may include acryl amide gel, gelatin, modified polyethylene glycol, modified polyvinyl pyrrolidone, modified polyethylene glycol and other hydrogels. The gel material should be such that a gel state is maintained in the conditions under which a ring probe is separated from cDNA and electrophoretically transferred. For example, in the conditions of Example 1, the gel material should be such that a gel state is maintained at 95° C.

In the Example, 0.5 mL of a solution containing 2% AWP (Toyo Gosei Co., Ltd.) and 10 mg/mL streptavidin in 50 mM tricine buffer (pH7.5) was added dropwise on the lower cover 202 and rotationally applied at a rate of 1500 rpm. Thereafter, the coating was irradiated with ultraviolet ray (2 mW/cm$^2$) including ray having a wavelength of 302 nm, for 2 minutes to gelatinize it. In this manner, a gel film 1401 having an immobilization site with streptavidin and having a thickness of about 10 μM was formed. Furthermore, a 1 μM solution of probe I (500 μL) having the 5' end modified with biotin was added dropwise so as to cover the gel film 1401, and allowed to react for 2 hours at room temperature while preventing dehydration. The gel film was washed with a sufficient amount of buffer, and the probe capable of hybridizing with the ring probe was immobilized to the gel film 1401.

The lower cover 202 having the gel film 1401 was attached to a reaction cell. On the resultant structure, the cDNA library sheet 1 was allowed to adhere and an upper cover 201 was provided. Then, 1 mL of 50 mM tricine buffer (pH7.5) was injected through an inlet 205 to the reaction cell, which was then deaerated.

Figure 15:
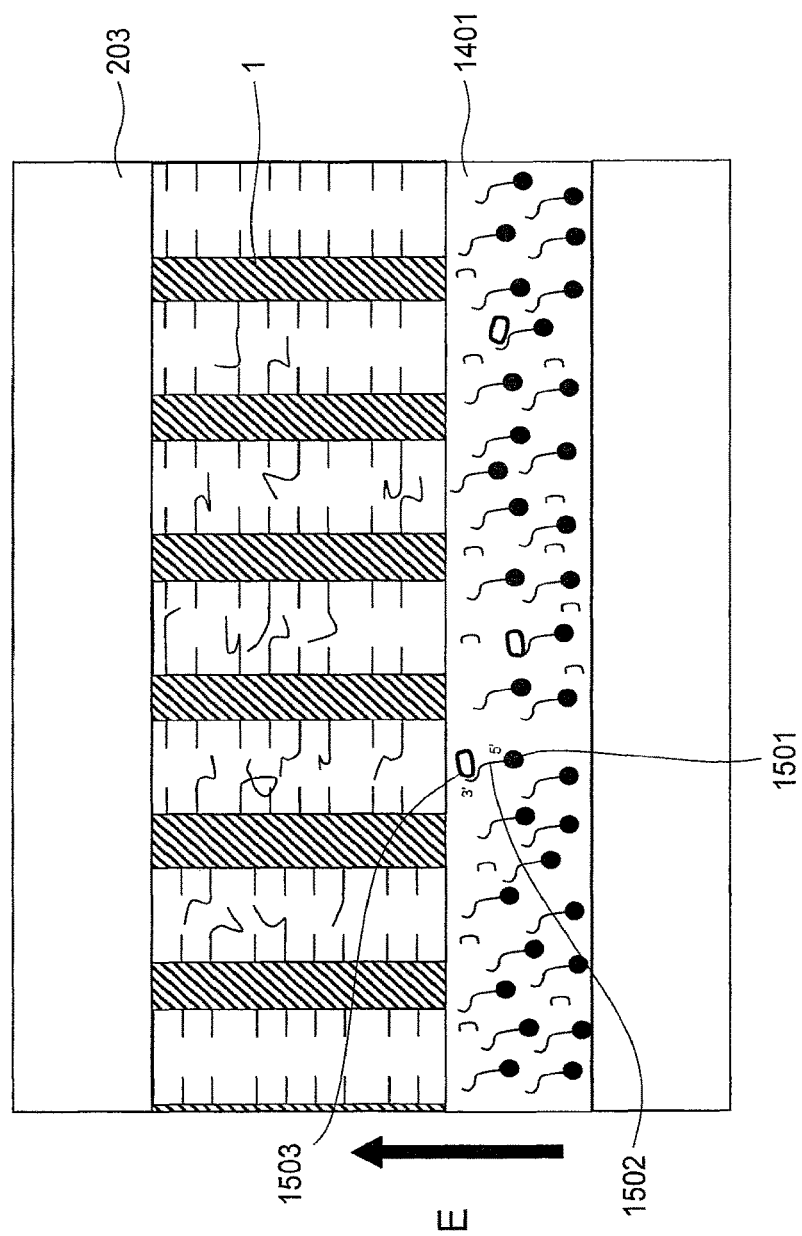
FIG. 15 shows a cross section of a pore array sheet and a gel film in the case where a ring probe is transferred to another gel film for detection and subjected to an RCA reaction.

Next, to prepare a ring probe within the sheet in the same manner as above, a reagent containing a padlock probe and ligase was injected through the inlet 205 and allowed to react in the conditions described in Example 1. To electrophoretically transfer the ring probe to the gel film, the gel film was heated at 95° C. for one minute while applying a voltage of +0.4V to an electrode inside the lower cover 202, and cooled at a rate of 1° C./sec up to 65° C. and kept for 10 minutes. The state of a section of the resultant gel film and the sheet was schematically shown in FIG. 15. 1501 represents streptavidin for immobilizing probe I (1502) via a biotin-avidin bond. Streptavidin and an AWP polymer are covalently bonded through a reaction between a primary amine of streptavidin and an azi group of the AWP polymer with the help of UV irradiation. The ring probe 1503 electrophoretically transferred is immobilized through hybridization with probe I (1502) highly densely immobilized.

Figure 16:
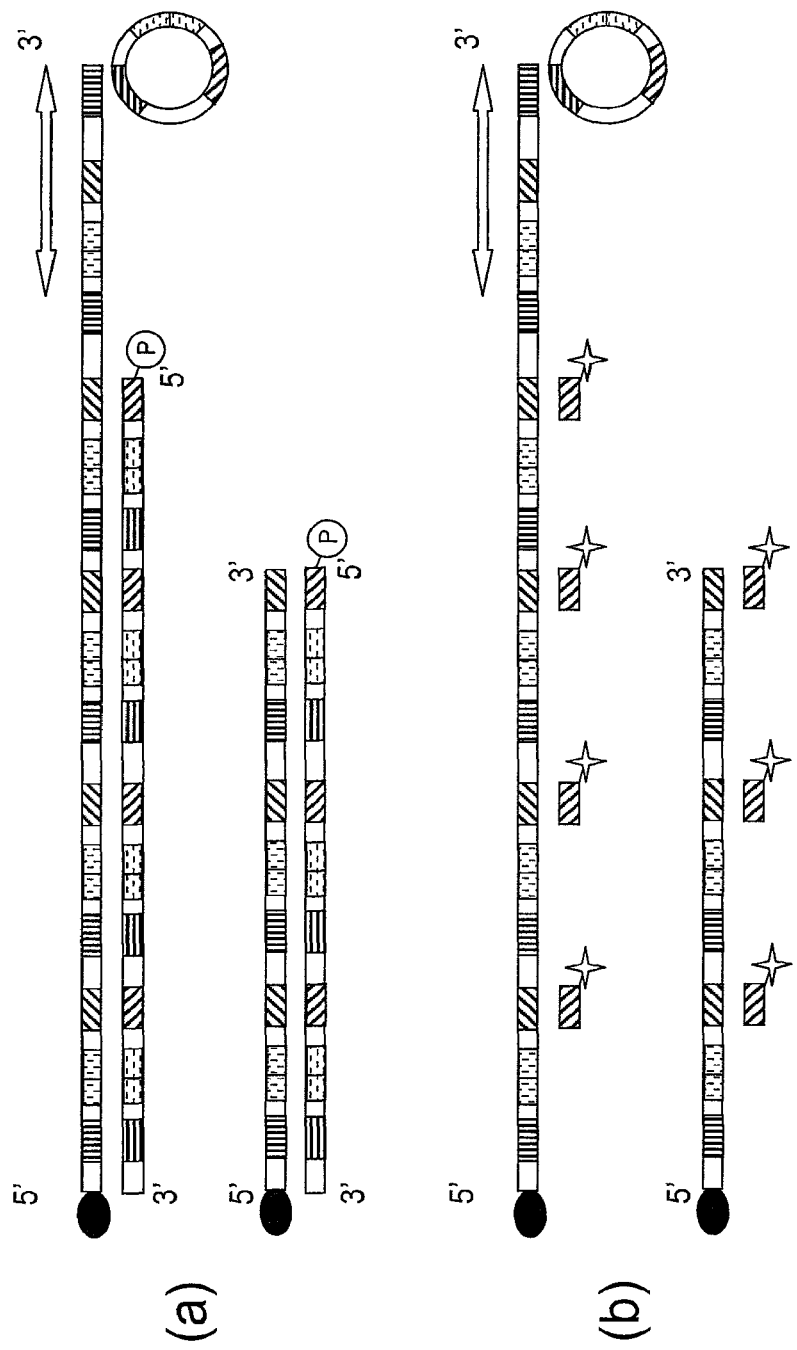
FIG. 16 schematically shows a rolling circle amplification (RCA) reaction in the case of measuring fluorescence.

Then, the cDNA library sheet was removed, and 100 μL of 10× φ29 luminescent reagent buffer (0.5 M Tricine, 0.1 M MgAc, 0.1 M (NH$_4$)$_2$SO$_4$, 4 mM DTT), 10 μL of free DNA probe II (0.1 μM) phosphorylated at the 5' end, 50 μL of 10 mM dNTP, 25 μL of 10 mg/mL BSA and 50 μL of 10 U/μL φ29 polymerase (New England BioLabs) were mixed with 775 μL of D.W. containing 10 mM DTT. The resultant mixture was injected through an inlet 205. Thereafter, while the reaction cell was kept at 37° C., an RCA reaction was performed for 60 minutes. The RCA reaction herein is the same as in Example 1. During the complementary strand synthesis reaction initiated from phosphorylated probe II, a plurality of complementary strands are separated from DNA extended from probe I by the strand displacement activity of φ29 polymerase; however, this strand comes to be trapped again by probe I in the proximity of a position at which the ring probe is initially hybridized with probe I, and a complementary strand synthesis reaction is initiated. Because of this, from a single molecule ring probe, a fluorescent spot derived from a plurality of strands each having hybridization sites for a plurality of fluorescent probes comes to be formed in the gel. The size of the fluorescent spot increases as the RCA reaction takes a longer time, as the concentration of probe II increases, and further, as the concentration of probe I decreases. In the aforementioned reaction conditions, the diameter of the spot was 0.1 to 0.3 μm. Furthermore, since considerably larger ratio of DNA chains are double-stranded, even if a fluorescent probe having a Cy3 fluorophore immobilized thereto and having the same sequence as that of probe II is introduced, the hybridization sites decreases. To prevent a decrease in fluorescence intensity due to this, a phosphorylated strand is selectively digested with lambda exonuclease to convert a double-strand into a single-strand. More specifically, as shown in FIG. 16(a), since a phosphate group is introduced into the 5' end, if the strand phosphorylated is digested with lambda exonuclease into a single-strand, a fluorescent probe can be bound to almost all sites, as shown in FIG. 16(b).

Next, to attach a fluorescent probe, probe (1 μM) having the same sequence as that of probe II and a fluorophore (Cy3) bound to the 5' end was injected into a reaction cell. After a voltage of +0.4 V was applied for 5 minutes, voltages of −0.4 V and +0.4 V were alternately applied at intervals of one minute to the lower cover 202. This operation was repeated three times. Thereafter, the solution was exchanged with a 50 mM tricine buffer containing no probe. While applying a voltage of −0.4V to the lower cover for 10 minutes, the buffer was continuously fed at a rate of 1 mL/min from the inlet 205 to the outlet 207.

Fluorescence was measured by the confocal optical system shown in FIG. 14. The structure of the optical system is the same as shown in FIG. 13. Fluorescent image of spots were obtained by scanning the gel in the z and xy directions. The refractive index distribution becomes smaller by use of gel compared to a pore array sheet, and thus scattered light rarely affect measurement of fluorescence.

Furthermore, fluorescence may be measured by using evanescent-excitation shown in FIG. 17. To attain evanescent-excitation, two hollows 1703 in the form of a right triangular prism were formed near the center of the lower cover 202 prepared of a quartz board having a thickness of 2 mm. Excitation light having a wavelength of 532 nm is enlarged 3 times by a laser beam expander 1202 and designed to converge on the border between the gel film 1401 and the upper surface of the lower cover 202 by a condenser lens 1702. At this time, laser light is refracted by the hollows 1703 and incident with an angle smaller than the critical angle of the aforementioned interface, and totally reflected. A region of only several hundreds of nms near the aforementioned interface is excited by the total reflection and the fluorophores present near the interface are measured.

The objective lens 1203 used herein had a NA of 0.8 and a working distance of 3.3 mm. A fluorescent image was obtained by using a cooled CCD camera 1206 as an image pickup device through a band pass filter 1207 which removes scattered light of excitation light and an imaging lens 1205.

In the Examples hereinabove, mRNA was quantified by counting fluorescent spots in a fluorescent image. Needless to say, quantification can be made based on the correlation between fluorescence intensity and the number of molecules. However, quantification based on the spot count is not only absolute quantification requiring no calibration curve but also the most accurate quantification method since only one single threshold is set in order to determine presence or absence of molecules. In contrast, in this method, spatial resolution is ignored. In the case where spatial resolution is required at the expense of quantification, quantification may be made based on the correlation between the intensity and the number of molecules. It may be understood that whether quantification is made based on the count or partly based on the intensity is a choice similarly applied to the case of chemiluminescence in Example 1.

Furthermore, to obtain a fluorescent image by evanescent-excitation, an objective lens for exclusive use of Total Internal Reflection Fluorescence (e.g., APON60×OTIRFM (Olympus Corporation)) may be used.

Also in this Example, needless to say, the cDNA library sheet can be repeatedly used. By overlaying a fluorescent image or a chemiluminescent image obtained in this method, a gene expression profile (gene expression distribution) obtained from the image and a microscopic image of the cell obtained in advance, data as to the correlation between a cell shape and gene expression can be obtained. This can be applied to all Examples. Furthermore, by overlaying an image obtained by a fluorescence in situ hybridization (FISH) method and an image obtained by the method of the invention, if the same gene is measured, quantification by the FISH method can be evaluated by taking advantage of highly accurate quantification of the method of the present invention.

Needless to say, as long as images can be overlaid, any fluorescent images and chemiluminescent images obtained by other labeling methods may be used.

Furthermore, light emission may be measured by use of a DNA probe having a chemiluminescent enzyme such as alkaline phosphatase and peroxidase immobilized thereto, in place of a fluorescent label, and thereafter, adding a chemiluminescent substrate.

Example 3

In this Example, unlike Example 1 or 2 in which a sheet having pores was used as a cDNA library sheet, another support such as a membrane was used to prepare a cDNA library.

As the membrane, a membrane rarely adsorbing a protein such as a cellulose acetate membrane, a nitrocellulose membrane or a membrane formed of a mixture of these and a nylon membrane can be available. In the Example, a case where a cellulose acetate membrane (Whatman) having a thickness of 115 μm, a pore size of 0.2 μm and a diameter of 25 mm will be described.

As shown in FIG. 18, to the surface of a membrane fiber 1802 within a membrane 1801, poly-T probes 1803 are immobilized by the silane coupling treatment in the same manner as in Example 1. At the same time, the MPC treatment is performed in the same manner. Next, the membrane is set in the same reaction cell as in Example 1 or 2. A tissue slice sample 1101 is mounted and the same treatments are performed. As a result, mRNA can be trapped by poly-T probes within the membrane while cell positional information is kept in the membrane. Thereafter, a reverse transcription reaction is performed in the same manner to prepare a cDNA library membrane.

A gene-specific fluorescent probe is introduced and quantified by the optical system capable of counting single molecules as shown in FIG. 13 or FIG. 14. In this manner, gene expression distribution may be determined. Alternatively, after chemical amplification such as RCA and PCR, fluorescence may be measured in the same manner as above.

Furthermore, similarly to Examples 1 and 2, a probe is transferred from a cDNA library sheet to a detection sheet (a pore sheet, a membrane and a gel film may be used for this) and then fluorescence and chemiluminescence may be measured without chemical amplification such as RCA and PCR. Alternatively, after amplification, the measurement may be performed in the same manner.

Furthermore, even if sheet-type gel films and other porous materials are used in place of a membrane, the same operation can be made.

Example 4

In this Example, a cDNA library was prepared by using beads as a support.

In this Example, beads smaller than cells are arranged on a surface. On the beads surface, poly-T probes are immobilized. On the resultant structure, a tissue slice is mounted and the same treatment as in the above Examples is performed. The sectional view of the cDNA library sheet in this case is shown in FIG. 19. On the upper surface of a quartz plate 1903, a transparent electrode 1902 was formed. On the resultant structure, Dynabeads 1901 of 1 μm in diameter having poly-T probes immobilized thereon were spread. A stopper 1904 was arranged at predetermined intervals so as not to move Dynabeads 1901. On the resultant structure, a tissue slice sample 1101 was mounted. Cells were lysed in the same manner as above and mRNA molecules were electrophoretically trapped on the surface of beads and reverse-transcribed to obtain a cDNA library sheet. As to measurement, since the quartz plate 1903 and the transparent electrode 1902 correspond to the lower cover 202, fluorescence can be measured through the quartz plate. If a porous material such as a nylon mesh is used in place of the quartz plate, the positional information of mRNA can be transferred to a sheet and a membrane separately provided. In the Example, beads are arranged in a single layer; however, beads may be arranged in multiple layers. Furthermore, the beads material may be a resin material such as polystyrene, a (metal) oxide such as glass, a metal, an organic material such as Sepharose and a mixture of these. For example, magnetic beads formed of polystyrene and iron in combination was used.

Next, as shown in FIG. 20, a number of beads are spread in the bottom of reaction cells in which cells are housed, and the same treatment may be performed. In the Example shown in the figure, 2001 represents the reaction cell. At the bottom thereof, magnetic beads 1901 of 1 μm in diameter having poly-T probes immobilized thereon were used. 1903 represents a quartz plate and 1902 represents a transparent electrode. These have the same function as mentioned above.

Example 5

In Examples 1 to 4, a gene-specific padlock probe was hybridized with cDNA and a gene-specifically formed ring probe was transferred to another sheet, membrane or gel. However, a method for transferring a gene expression distribution to another membrane is not limited to this method.

For example, when cDNA is synthesized from mRNA by use of M-MLV reverse transcriptase (e.g., SUPERSCRIPT II) as the reverse transcriptase, a CCC sequence can be added to all ends of cDNA. Subsequently, a probe capable of recognizing this sequence is hybridized to it within the sheet. After an extension reaction, a complementary strand having an appropriate length is transferred to another sheet. In this manner, distribution data of all cDNAs can be transferred to another sheet.

When data of all gene expression are subjected to sequence analysis, a distribution can be obtained. At this time, if a pyro-sequencing method is used, conversion to a sequence from which a homo polymer is eliminated can be made.

Figure 21:
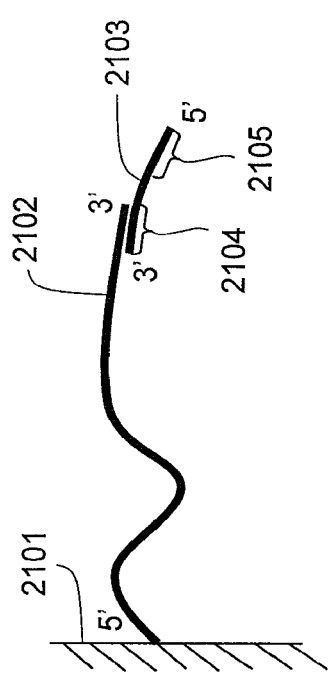
FIG. 21 shows an example of a probe design for use in detecting a target cDNA in a cDNA library.

Furthermore, hybridization of a gene-specific probe, which does not form a ring, is performed and the corresponding sequence to the genetic information is attached to the 5' end, as shown in FIG. 21. In this manner, data can be retained by a sequence different from a target sequence. In FIG. 21, 2101 represents a pore inner wall of a sheet or a fiber of a membrane. To the surface, a cDNA library is immobilized. 2102 represents a single-stranded cDNA. To a part thereof, a DNA probe 2103 is sequence-specifically hybridized. The sequence specificity is due to the fact that a sequence 2104 is complementary to a part of the cDNA sequence. By arranging a known sequence corresponding to this sequence, for example, at a position represented by 2105, fluorescence and chemiluminescence measurement by recognizing the sequence, which is not the sequence of an original cDNA, can be achieved. If a common sequence portion is introduced into such a probe, since a primer is hybridized with the common sequence portion and amplified, amplification bias can be reduced as is the same as in the aforementioned Examples. If a universal base is employed in the sequence recognition portion 2104, a certain group of sequences can be represented by a single sequence and a single probe can be reacted with genes of the group.

Example 6

In the aforementioned Examples, fluorescence and chemiluminescence measurements were employed; however, mRNA distribution can be quantitatively determined by measuring a potential change of an electrode, which is caused by proximity of DNA to an electrode surface. Particularly, by using a potential change of a gate electrode of FET, a DNA probe transcribed from a cDNA library sheet can be quantified. If the capacity of the gate electrode is reduced up to about fF, since movement of a single elementary charge near the gate electrode can be measured, hybridization of a single DNA molecule on the gate electrode can be measured.

Figure 22:
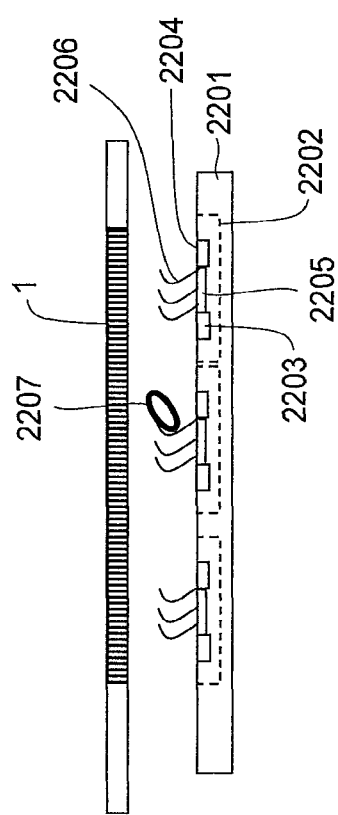
FIG. 22 shows an example of a method for measuring gene expression by potential measurement.

FIG. 22 shows an example of the structure of a measurement apparatus based on potential measurement. 1 represents a pore array sheet in which a cDNA library has been formed. Right under the sheet, a semiconductor chip 2201 having a number of FETs arranged thereon is disposed so as to be almost in contact therewith. The space between the FET chip 2201 and the sheet 1, and the interior portion of the sheet 1 are filled with an electrolyte solution, and the potential of the solution is controlled by a reference electrode. A large number of FET cells 2202 are formed on the chip. A single source 2203, drain 2204 and gate 2205 are formed per cell. Size of a cell is set to be 1 μm. A word line and a lead line are formed between cells. The current between the source and drain in a specific cell can be sequentially measured by plural of switching FETs. The gate electrode is formed of polysilicon wiring of 50 nm in width. Gate-drain and gate-ground capacities are designed to be sufficiently low. On the gate electrode, a probe 2206 capable of specifically hybridizing with a ring-form probe 2207 is immobilized with a silane coupling agent. Since the gate-electrode potential reduces by the presence of negative ions due to hybridization, the current between the source and drain can be efficiently changed.

Example 7

In the aforementioned Examples, a method of quantifying the distribution of mRNA has been described in detail. The same method can be applied also to non-coding RNA (ncRNA) and genomic DNA, other than mRNA. The difference resides in that not a poly-T probe but a universal probe is used. The universal probe, which is capable of immobilizing a target sequence (ncRNA and DNA etc.) to be analyzed, may be immobilized on the inner wall of pores of a sheet or a fiber of a membrane.

Example 8

In this Example, the presence of a molecule (for example, protein or other low-molecule weight substances) other than a nucleic acid is analyzed. An antibody or aptamer, which specifically binds to a molecule to be quantified within a cell, is immobilized within a pore to form a ring probe specific to the molecule to be quantified, and distribution of the presence of the molecule within the cell can be quantified in the same manner as in the aforementioned Examples. This method is called a Proximity Ligation Method (see, Malin Jarvius et al. Molecular & Cellular Proteomics 6 (9) p. 1500, 2007).

Figure 23:
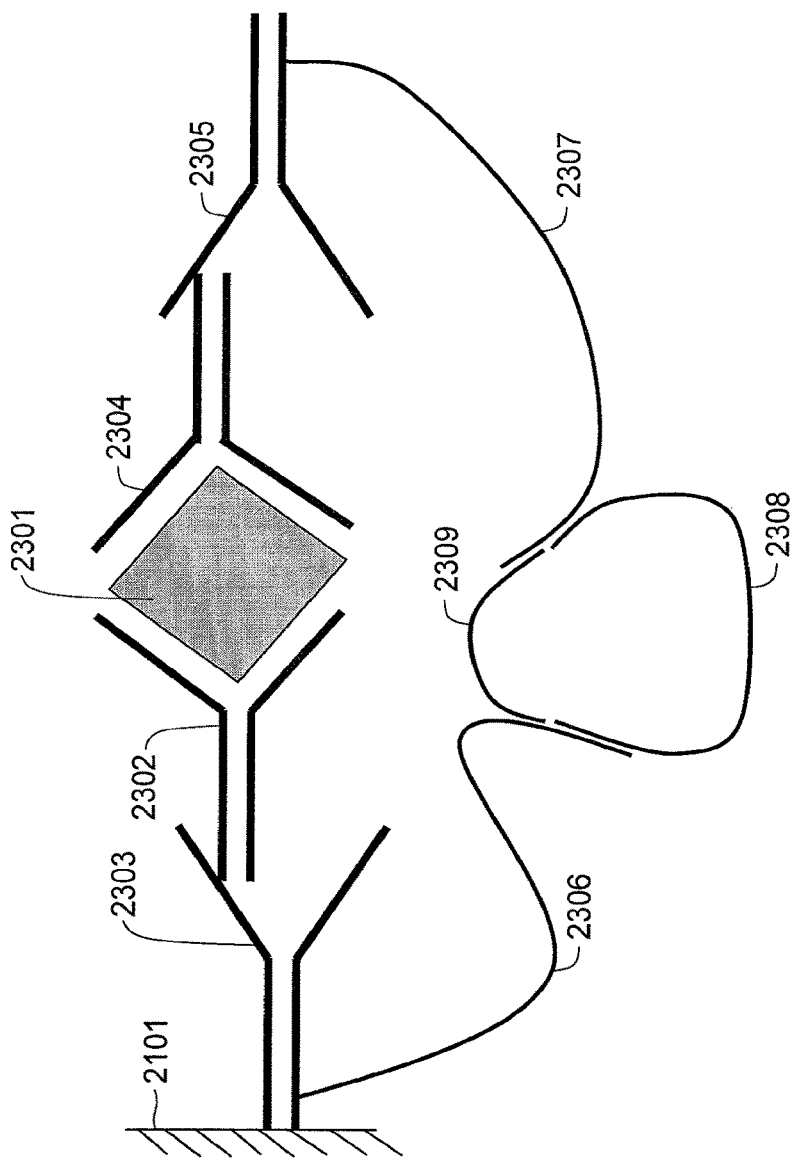
FIG. 23 shows an example of a method for immobilizing a molecule to be determined to a cDNA library by use of a proximity ligation method and quantifying it.

FIG. 23 shows a schematic view of the interior of a pore of a sheet. 2101 represents an inner wall of a pore or a fiber of a membrane. An antibody 2302, which is capable of binding to a molecule 2301 to be quantified within a cell, is immobilized by immobilizing a secondary antibody 2303, which recognizes the antibody as an antigen, onto the pore wall surface 2101. As a result, the molecule 2301 to be quantified is immobilized. Furthermore, the molecule 2301 to be quantified is sandwiched between antibody 2302 and another antibody 2304, to which a secondary antibody 2305 capable of recognizing the antibody is bound. To the aforementioned secondary antibodies, DNAs (2306 and 2307) are respectively immobilized. When the molecule 2301 to be quantified is bound to the antibodies 2302 and 2304, these two single-stranded DNAs come closer. At this time, two DNA probes 2308 and 2309 are injected into a pore to hybridize with the DNAs 2306 and 2307. A ring probe is formed through a ligation reaction. After the ring probe is formed, measurement is performed in accordance with the same method as described in the aforementioned Examples.

All publications, patents and patent applications cited in the specification are incorporated in its entirety in this specification by reference.

INDUSTRIAL APPLICABILITY

The present invention provides a method for analyzing a gene expression profile. The method of the present invention enables to detect expression of a gene in a sample with its two-dimensional positional information. Furthermore, in the method of the present invention, since genes expressed in a sample are all converted into cDNAs to construct a cDNA library, gene expression can be simply and efficiently detected. Therefore, the present invention is useful in the fields of e.g., cell function analysis, biotissue analysis, diagnosis for diseases and drug development.

EXPLANATION OF NUMERALS

1 Sheet
2 Pore
3 Cell
4 Gel containing cell lysis reagent
5 mRNA
6 Pore
7 DNA probe
8 mRNA trapped in pore
9 cDNA
10 Probe
201 Upper cover, Upper electrode
202 Lower cover, Lower electrode
203 Upper reaction region
204 Lower reaction region
205 Inlet
206 Upper outlet
207 Lower outlet
209 Spacer
210 Immobilization jig
211 Screw
212 Protection ring
220 Upper outlet
221 Lower outlet
801 Sheet
901 Objective lens
902 Imaging lens
903 Cooled CCD camera
1001 Slit
1002 Avalanche photodiode (APD) or photomultiplier tube (PMT)
1101 Tissue slice sample
1201 Laser
1202 Laser beam expander
1203 Objective lens
1204 Dichroic mirror
1205 Imaging lens
1206 Cooled CCD camera
1207 Band pass filter
1210 xyz direction
1301 Pin hole
1302 Light detector
1401 Gel film
1501 Streptavidin
1502 Probe I
1503 Ring probe
1701 Mirror
1702 Condenser lens
1703 Hollow
1801 Membrane
1802 Membrane fiber
1803 Probe
1901 Dynabeads or magnetic beads
1902 Transparent electrode
1903 Plate
1904 Stopper
2001 Reaction cell
2101 Pore inner wall of sheet or fiber of membrane
2102 cDNA
2103 DNA probe
2104 Sequence complementary to a part of cDNA
2105 Known sequence different from cDNA sequence
2201 Semiconductor chip or FET chip
2202 FET cell
2203 Source
2204 Drain
2205 Gate
2206 Probe
2207 Ring probe
2301 Molecule to be quantified
2302 Antibody
2303 Secondary antibody
2304 Antibody
2305 Secondary antibody
2306 DNA
2307 DNA
2308 DNA probe
2309 DNA probe
2601 One-shot image taken by a CCD camera
2602 Fluorescent spots
2603 A plurality of sites
2604 xyz direction
2605 A set of data

FREE TEXT FOR SEQUENCES

SEQ ID NOs: 1-4: Artificial (synthetic DNA)

What is claimed is:

1. An analysis apparatus, comprising:
a test nucleic acid and a nucleic acid extraction reagent;
a support where a test nucleic acid-capturing part has been two-dimensionally distributed, wherein the test nucleic acid-capturing part is on the surface of and/or within a plurality of pores perpendicular to the support;
a nucleic acid probe of the test nucleic acid-capturing part;
a captured test nucleic acid having a complementary strand;
an enzyme for synthesizing the complementary strand;
a channel for feeding at least test nucleic acids and reagents into the apparatus;
an optical system for conducting an analysis of the test nucleic acid;
a cell on the plurality of pores perpendicular to the support; and
a cDNA library,
wherein the test nucleic acid-capturing part comprises the nucleic acid probe immobilized thereto, and the nucleic acid probe being positioned below the cell on the support;
wherein the nucleic acid probe is capable of capturing the test nucleic acid that is considered captured by virtue of its interaction with the nucleic acid probe and the test nucleic acid on the plurality of pores perpendicular to the support; and
wherein the cDNA library on the support is a product of synthesis of the complementary strand of the captured test nucleic acid by the enzyme for synthesizing the complementary strand.

2. The apparatus of claim 1, wherein the optical system is configured to obtain lateral positional information of the test nucleic acid on the support, which has been captured to the nucleic acid-capturing part of the support.

3. The apparatus of claim 2, wherein the optical system is configured to analyze gene expression profile for the cell based on the lateral positional information of the test nucleic acid.

4. The apparatus of claim 3, wherein the optical system is configured to analyze gene expression profile for each of a plurality of the cells, and compares the gene expression profiles of the cells.

5. The apparatus of claim 1, wherein the optical system is configured to optically analyze lateral positional information of the test nucleic acid of the support, which has been captured to the nucleic acid-capturing part.

6. The apparatus of claim 2, wherein the optical system is configured to analyze the correlation between a cell shape and gene expression based on a microscopic image of the cell and the lateral positional information of the test nucleic acid.

7. The apparatus of claim 1, wherein the test nucleic acid is messenger RNA (mRNA).

8. The apparatus of claim 7, wherein the test nucleic acid-capturing part of the support comprises a DNA probe containing a poly-T sequence immobilized thereto as the nucleic acid probe.

9. The apparatus of claim 1, wherein the support is at least one selected from the group consisting of a sheet, a membrane, a gel thin film, a capillary plate and packed beads.

10. The apparatus of claim 1, wherein the support is a porous sheet, and the test nucleic acid-capturing part is a pore of 20 nm to 200 nm in diameter, and wherein the nucleic acid probe is immobilized to the pore which is perpendicular to the support.

11. A device, comprising:
a test nucleic acid and a nucleic acid extraction reagent;
a support where a test nucleic acid-capturing part has been two-dimensionally distributed, wherein the test nucleic acid-capturing part is on the surface of and/or within a plurality of pores perpendicular to the support;
a nucleic acid probe of the test nucleic acid-capturing part;
a captured test nucleic acid having a complementary strand;
an enzyme for synthesizing the complementary strand;
a channel for feeding at least test nucleic acids and reagents into the apparatus;
a cell on the support; and
a cDNA library;
wherein the test nucleic acid-capturing part comprises the nucleic acid probe immobilized thereto, and the nucleic acid probe is positioned below the cell on the support;
wherein the nucleic acid probe is configured to capture the captured test nucleic acid that is considered captured by virtue of an interaction with the nucleic acid probe and the cDNA library on the plurality of pores perpendicular to the support; and
wherein the cDNA library on the pores perpendicular to the support is a product of synthesis of the complementary strand of the captured test nucleic acid by the enzyme for synthesizing the complementary strand.

12. The device of claim 11, wherein the test nucleic acid is messenger RNA (mRNA).

13. The device of claim 12, wherein the test nucleic acid-capturing part of the support comprises a DNA probe containing a poly-T sequence immobilized thereto as the nucleic acid probe.

14. The device of claim 11, wherein the support is at least one selected from the group consisting of a sheet, a membrane, a gel thin film, a capillary plate and packed beads.

15. The device of claim 11, wherein the support is a porous sheet, and the test nucleic acid-capturing part is a pore of 20 nm to 200 nm in diameter, and wherein the nucleic acid probe is immobilized to the pore which is perpendicular to the support.

* * * * *

SEQUENCE LISTING

<160> NUMBER OF SEQ ID NOS: 4

<210> SEQ ID NO 1
<211> LENGTH: 1310
<212> TYPE: DNA
<213> ORGANISM: Artificial
<220> FEATURE:
<223> OTHER INFORMATION: synthetic DNA

<400> SEQUENCE: 1

| | | | | | |
|---|---|---|---|---|---|
| aaattgagcc | cgcagcctcc | cgcttcgctc | tctgctcctc | ctgttcgaca | gtcagccgca | 60 |
| tcttcttttg | cgtcgccagc | cgagccacat | cgctcagaca | ccatggggaa | ggtgaaggtc | 120 |
| ggagtcaacg | gatttggtcg | tattgggcgc | ctggtcacca | gggctgcttt | taactctggt | 180 |
| aaagtggata | ttgttgccat | caatgacccc | ttcattgacc | tcaactacat | ggtttacatg | 240 |
| ttccaatatg | attccaccca | tggcaaattc | catggcaccg | tcaaggctga | gaacgggaag | 300 |
| cttgtcatca | atggaaatcc | catccaccat | ttccaggagc | gagatccctc | caaaatcaag | 360 |
| tggggcgatg | ctggcgctga | gtacgtcgtg | gagtccactg | gcgtcttcac | caccatggag | 420 |
| aaggctgggg | ctcatttgca | gggggagcc | aaaagggtca | tcatctctgc | ccctctgct | 480 |
| gatgccccca | tgttcgtcat | gggtgtgaac | catgagaagt | atgacaacag | cctcaagatc | 540 |
| atcagcaatg | cctcctgcac | caccaactgc | ttagcacccc | tggccaaggt | catccatgac | 600 |
| aactttggta | tcgtggaagg | actcatgacc | acagtccatg | ccatcactgc | cacccagaag | 660 |
| actgtggatg | gccctccgg | gaaactgtgg | cgtgatggcc | gcggggctct | ccagaacatc | 720 |
| atccctgcct | ctactggcgc | tgccaaggct | gtgggcaagg | tcatccctga | gctgaacggg | 780 |
| aagctcactg | gcatggcctt | ccgtgtcccc | actgccaacg | tgtcagtggt | ggacctgacc | 840 |
| tgccgtctag | aaaaacctgc | caaatatgat | gacatcaaga | aggtggtgaa | gcaggcgtcg | 900 |
| gagggccccc | tcaagggcat | cctgggctac | actgagcacc | aggtggtctc | ctctgacttc | 960 |
| aacagcgaca | cccactcctc | cacctttgac | gctggggctg | gcattgccct | caacgaccac | 1020 |
| tttgtcaagc | tcatttcctg | gtatgacaac | gaatttggct | acagcaacag | ggtggtggac | 1080 |
| ctcatggccc | acatggcctc | caaggagtaa | gaccctgga | ccaccagccc | cagcaagagc | 1140 |
| acaagaggaa | gagagagacc | ctcactgctg | gggagtccct | gccacactca | gtcccccacc | 1200 |
| acactgaatc | tcccctcctc | acagttgcca | tgtagacccc | ttgaagaggg | gaggggccta | 1260 |
| gggagccgca | ccttgtcatg | taccatcaat | aaagtaccct | gtgctcaacc | | 1310 |

<210> SEQ ID NO 2
<211> LENGTH: 110
<212> TYPE: DNA
<213> ORGANISM: Artificial
<220> FEATURE:
<223> OTHER INFORMATION: synthetic DNA

<400> SEQUENCE: 2

| | | | | | |
|---|---|---|---|---|---|
| tcatgaccac | agtccatgcc | atcactgcca | cccagaagac | tgtggatggc | cctccgctt | 60 |
| agcacccctg | ccaaggtca | tccatgacaa | ctttggtatc | gtggaaggac | | 110 |

<210> SEQ ID NO 3
<211> LENGTH: 42
<212> TYPE: DNA
<213> ORGANISM: Artificial
<220> FEATURE:
<223> OTHER INFORMATION: synthetic DNA -continued

```
<400> SEQUENCE: 3
tctctctctc tctctctctc agtcttctgg gtggcagtga tg                    42

<210> SEQ ID NO 4
<211> LENGTH: 22
<212> TYPE: DNA
<213> ORGANISM: Artificial
<220> FEATURE:
<223> OTHER INFORMATION: synthetic DNA

<400> SEQUENCE: 4
cacccctggc caaggtcatc ca                                          22
```